US012103020B2

United States Patent
Gruenbacher et al.

(10) Patent No.: US 12,103,020 B2
(45) Date of Patent: Oct. 1, 2024

(54) MICROFLUIDIC DELIVERY DEVICE AND METHOD FOR DISPENSING A FLUID COMPOSITION UPWARD INTO THE AIR

(71) Applicant: The Procter & Gamble Company, Cincinnati, OH (US)

(72) Inventors: Dana Paul Gruenbacher, Fairfield, OH (US); Stephan Gary Bush, Liberty Township, OH (US); Hua Hu, Mason, OH (US); William Paul Mahoney, III, Liberty Township, OH (US); Steven Robert Komplin, Lexington, KY (US); Jason Todd Vanderpool, Lexington, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 256 days.

(21) Appl. No.: 15/936,469

(22) Filed: Mar. 27, 2018

(65) Prior Publication Data
US 2018/0290156 A1    Oct. 11, 2018

Related U.S. Application Data

(60) Provisional application No. 62/483,496, filed on Apr. 10, 2017.

(51) Int. Cl.
*B05B 1/26*     (2006.01)
*A61L 9/12*     (2006.01)
(Continued)

(52) U.S. Cl.
CPC .............. *B05B 1/267* (2013.01); *A61L 9/122* (2013.01); *A61L 9/14* (2013.01); *B05B 1/24* (2013.01);
(Continued)

(58) Field of Classification Search
CPC ...... A61L 9/14; A61L 9/122; A61L 2209/133; A61L 2209/132; A61L 9/037; A61L 9/04;
(Continued)

(56) References Cited

U.S. PATENT DOCUMENTS

| 3,181,750 A | 5/1965 | Helliwell |
| 3,465,350 A | 9/1969 | Keur et al. |

(Continued)

FOREIGN PATENT DOCUMENTS

| CA | 2213066 A1 | 2/1999 |
| CN | 1393491 A | 1/2003 |

(Continued)

OTHER PUBLICATIONS

U.S. Appl. No. 15/936,471, filed Mar. 27, 2018, Gruenbacher, et al.
(Continued)

*Primary Examiner* — Dean Kwak
(74) *Attorney, Agent, or Firm* — Carolyn S. Powell; George H. Leal; Abby Alicia Lopez

(57) ABSTRACT

A microfluidic delivery device and method of dispensing a fluid composition therefrom is provided. The microfluidic delivery device includes a housing electrically connectable with a power source; a cartridge releasably connectable with the housing; and a fan connected with the housing. The cartridge has a reservoir for containing a fluid composition and microfluidic die in fluid communication with the reservoir. The die is configured such that substantially all of the fluid composition exits the microfluidic die in a horizontal direction or downward direction relative to horizontal. The fan is configured to generate air flow that converges with and redirects the fluid composition dispensed from the microfluidic die in an upward direction relative to horizontal.

7 Claims, 18 Drawing Sheets

(51) Int. Cl.
  *A61L 9/14*    (2006.01)
  *B05B 1/24*    (2006.01)
  *B05B 17/00*   (2006.01)
  *B05B 17/06*   (2006.01)

(52) U.S. Cl.
  CPC ...... *B05B 17/0638* (2013.01); *B05B 17/0684* (2013.01); *A61L 9/127* (2013.01); *A61L 2209/132* (2013.01); *A61L 2209/133* (2013.01)

(58) Field of Classification Search
  CPC .... A61L 2209/111; A61L 9/035; A61L 9/048; A61L 9/127; A61L 2209/11; A61L 9/03; A61L 9/12; A61L 9/125; A61L 2209/131; A61L 9/032; A61L 9/16; A61L 2209/134; A61L 2209/135; A61L 9/014; A61L 9/042; A61L 15/20; A61L 15/28; A61L 15/46; A61L 2209/14; A61L 2209/21; A61L 2300/62; A61L 2/18; A61L 9/01; A61L 9/012; A61L 9/02; B05B 17/0684; B05B 17/0646; B05B 1/24; B05B 17/0638; B05B 17/0669; B05B 1/267; B05B 3/001; B05B 5/001; B05B 7/0815; B05B 7/0081; B05B 7/1666; B05B 9/002
  See application file for complete search history.

(56) References Cited

U.S. PATENT DOCUMENTS

| | | |
|---|---|---|
| 3,465,351 A | 9/1969 | Keur et al. |
| 3,967,286 A | 6/1976 | Andersson et al. |
| 4,532,530 A | 7/1985 | Hawkins |
| 5,084,713 A | 1/1992 | Wong |
| 5,317,339 A | 5/1994 | Braun et al. |
| 5,591,409 A | 1/1997 | Watkins |
| 5,610,635 A | 3/1997 | Murray et al. |
| 5,665,278 A | 9/1997 | Allen et al. |
| 5,666,140 A | 9/1997 | Mitani |
| 5,714,989 A | 2/1998 | Wade et al. |
| 5,819,756 A | 10/1998 | Mielordt |
| 5,874,974 A | 2/1999 | Courian et al. |
| 5,975,675 A | 11/1999 | Kim |
| 6,010,210 A | 1/2000 | Wilson et al. |
| 6,012,799 A | 1/2000 | Silverbrook |
| 6,024,440 A | 2/2000 | Murthy et al. |
| 6,113,228 A | 9/2000 | Pawlowski, Jr. et al. |
| 6,126,277 A | 10/2000 | Feinn et al. |
| 6,139,131 A | 10/2000 | Prasad et al. |
| 6,170,937 B1 | 1/2001 | Childers et al. |
| 6,261,347 B1 | 7/2001 | Moreland |
| 6,282,458 B1 | 8/2001 | Murayama et al. |
| 6,287,550 B1 | 9/2001 | Trinh et al. |
| 6,322,200 B1 | 11/2001 | Feinn et al. |
| 6,325,475 B1 | 12/2001 | Hayes et al. |
| 6,371,451 B1 | 4/2002 | Choi |
| 6,543,887 B2 | 4/2003 | Chang et al. |
| 6,672,129 B1 | 1/2004 | Frederickson et al. |
| 6,698,862 B1 | 3/2004 | Choi et al. |
| 6,808,684 B2 | 10/2004 | Boden et al. |
| 6,824,083 B2 | 11/2004 | Okuda et al. |
| 6,834,937 B2 | 12/2004 | Killmeier et al. |
| 7,011,795 B2 | 3/2006 | Thompson et al. |
| 7,097,263 B2 | 8/2006 | Silverbrook |
| 7,147,170 B2 | 12/2006 | Nguyen et al. |
| 7,201,916 B2 | 4/2007 | Schiavo et al. |
| 7,223,361 B2 | 5/2007 | Kvietok et al. |
| 7,293,849 B2 | 11/2007 | Tani et al. |
| 7,328,974 B2 | 2/2008 | Wang |
| 7,360,724 B2 | 4/2008 | Willey et al. |
| 7,367,661 B2 | 5/2008 | Hess et al. |
| 7,389,972 B2 | 6/2008 | Mathias |
| 7,490,815 B2 | 2/2009 | Tollens et al. |
| 7,499,632 B2 | 3/2009 | Granger et al. |
| 7,503,668 B2 | 3/2009 | Porchia |
| 7,669,978 B2 | 3/2010 | Spivey |
| 7,938,974 B2 | 5/2011 | McAvoy et al. |
| 7,954,934 B2 | 6/2011 | Shinada et al. |
| 8,020,573 B2 | 9/2011 | Lamers et al. |
| 8,087,759 B2 | 1/2012 | Oikawa et al. |
| 8,109,609 B2 | 2/2012 | Shim et al. |
| 8,142,558 B2 | 3/2012 | Robertson et al. |
| 8,201,752 B2 | 6/2012 | Brodbeck et al. |
| 8,251,500 B2 | 8/2012 | Yamada et al. |
| 8,338,346 B2 | 12/2012 | Diersing et al. |
| 8,430,484 B2 | 4/2013 | Fang |
| 8,821,802 B2 | 9/2014 | Haran |
| 8,870,090 B2 | 10/2014 | Feriani et al. |
| 8,881,999 B2 | 11/2014 | Blaylock et al. |
| 8,955,522 B1 | 2/2015 | Bowen |
| 9,072,841 B2 | 7/2015 | Thueer et al. |
| 9,156,263 B2 | 10/2015 | Kodoi et al. |
| 9,174,445 B1 | 11/2015 | Prati |
| 9,174,453 B1 | 11/2015 | Dodd et al. |
| 9,211,356 B2 | 12/2015 | Gruenbacher et al. |
| 9,211,980 B1 | 12/2015 | Gruenbacher et al. |
| 9,377,786 B2 | 6/2016 | Nakamoto et al. |
| 9,408,416 B2 | 8/2016 | Monsees |
| 9,554,459 B2 | 1/2017 | Gruenbacher et al. |
| 9,585,981 B2 | 3/2017 | Wynalda, Jr. |
| 9,586,228 B2 | 3/2017 | Roemburg et al. |
| 9,636,430 B2 | 5/2017 | Gruenbacher et al. |
| 9,763,478 B2 | 9/2017 | Cameron |
| 9,936,736 B2 | 4/2018 | Cameron |
| 9,943,116 B2 | 4/2018 | Cameron |
| 10,039,327 B2 | 8/2018 | Cameron |
| 10,058,128 B2 | 8/2018 | Cameron |
| 10,065,138 B2 | 9/2018 | Blackley |
| 10,085,486 B2 | 10/2018 | Cameron |
| 10,104,915 B2 | 10/2018 | Bowen |
| 10,118,391 B2 | 11/2018 | Dodd |
| 10,123,491 B2 | 11/2018 | De Fazio |
| 10,127,741 B2 | 11/2018 | Cameron |
| 10,212,971 B2 | 2/2019 | Cameron |
| 10,729,800 B2 | 8/2020 | Fujita et al. |
| 2001/0050317 A1 | 12/2001 | Denen |
| 2002/0005878 A1 | 1/2002 | Moon et al. |
| 2002/0043568 A1 | 4/2002 | Hess |
| 2002/0050533 A1 | 5/2002 | Hirota et al. |
| 2002/0063752 A1 | 5/2002 | Clark |
| 2002/0068010 A1 | 6/2002 | Laudamiel-Pellet et al. |
| 2002/0086319 A1 | 7/2002 | Ellson et al. |
| 2002/0092918 A1 | 7/2002 | Anderson |
| 2002/0192255 A1 | 12/2002 | Schiavo et al. |
| 2003/0062385 A1 | 4/2003 | Engel et al. |
| 2003/0218077 A1 | 11/2003 | Boticki et al. |
| 2004/0119793 A1 | 6/2004 | Mutz et al. |
| 2004/0200907 A1 | 10/2004 | Martens, III et al. |
| 2004/0032468 A1 | 12/2004 | Killmeier et al. |
| 2005/0018016 A1 | 1/2005 | Silverbrook |
| 2005/0037945 A1 | 2/2005 | Gygax et al. |
| 2005/0062804 A1 | 3/2005 | Eaton |
| 2005/0077376 A1 | 4/2005 | Hess et al. |
| 2005/0091879 A1 | 5/2005 | DuVal et al. |
| 2005/0124512 A1 | 6/2005 | Woo et al. |
| 2005/0128265 A1 | 6/2005 | Jones |
| 2005/0147523 A1 | 7/2005 | Laudamiel-Pellet et al. |
| 2005/0205916 A1 | 9/2005 | Conway et al. |
| 2005/0279854 A1 | 12/2005 | Martens, III et al. |
| 2006/0001737 A1 | 1/2006 | Dawson et al. |
| 2006/0011737 A1 | 1/2006 | Amenos |
| 2006/0065755 A1 | 3/2006 | Sugita et al. |
| 2006/0146126 A1 | 7/2006 | Guo |
| 2006/0152550 A1 | 7/2006 | Tomita et al. |
| 2006/0256168 A1 | 11/2006 | Einat |
| 2006/0280665 A1 | 12/2006 | Rees et al. |
| 2007/0008380 A1 | 1/2007 | Ushinohama et al. |
| 2007/0010645 A1 | 1/2007 | Vonwiller et al. |
| 2007/0166575 A1 | 7/2007 | Mcleod |
| 2007/0207174 A1 | 9/2007 | Pluyter et al. |
| 2007/0222830 A1 | 9/2007 | Moynihan |
| 2008/0023569 A1 | 1/2008 | O'Leary et al. |
| 2008/0043063 A1 | 2/2008 | Bergstedt et al. |

(56) References Cited

U.S. PATENT DOCUMENTS

| | | |
|---|---|---|
| 2008/0061163 A1 | 3/2008 | Kubby et al. |
| 2008/0073443 A1 | 3/2008 | Tollens et al. |
| 2008/0136868 A1 | 6/2008 | Lebens |
| 2008/0197213 A1 | 8/2008 | Flashinski et al. |
| 2009/0056289 A1* | 3/2009 | Miyazaki .............. B01D 50/002 55/332 |
| 2009/0096839 A1 | 4/2009 | Olbrich et al. |
| 2009/0108094 A1 | 4/2009 | Ivri |
| 2009/0121043 A1 | 5/2009 | Jean et al. |
| 2009/0126722 A1 | 5/2009 | Sugita et al. |
| 2009/0127297 A1 | 5/2009 | Zirps |
| 2009/0289127 A1 | 11/2009 | Tollens et al. |
| 2009/0308945 A1 | 12/2009 | Loverich et al. |
| 2010/0044453 A1 | 2/2010 | Porchia |
| 2010/0154790 A1 | 6/2010 | Merassi et al. |
| 2010/0206306 A1 | 8/2010 | Feriani et al. |
| 2010/0328957 A1 | 12/2010 | Hessing |
| 2011/0024521 A1 | 2/2011 | Jorgensen |
| 2011/0036365 A1 | 2/2011 | Chong et al. |
| 2011/0049266 A1 | 3/2011 | Jorgensen |
| 2011/0089252 A1 | 4/2011 | Rosener et al. |
| 2011/0130877 A1 | 6/2011 | Lynch |
| 2011/0221083 A1 | 9/2011 | Laulicht et al. |
| 2011/0284653 A1 | 11/2011 | Butler et al. |
| 2011/0284656 A1 | 11/2011 | Kambayashi et al. |
| 2011/0290911 A1 | 12/2011 | Tollens et al. |
| 2012/0093491 A1 | 4/2012 | Browder et al. |
| 2012/0097754 A1 | 4/2012 | Vlad et al. |
| 2013/0010035 A1 | 1/2013 | Norikane et al. |
| 2013/0026250 A1 | 1/2013 | Burt et al. |
| 2013/0042865 A1 | 2/2013 | Monsees |
| 2013/0050315 A1 | 2/2013 | Kusakari |
| 2013/0079733 A1 | 3/2013 | Burt et al. |
| 2013/0083126 A1 | 4/2013 | Dokyi et al. |
| 2013/0206857 A1 | 8/2013 | Ivri |
| 2013/0292484 A1 | 11/2013 | Jackson et al. |
| 2014/0034748 A1 | 2/2014 | Adair et al. |
| 2014/0043388 A1 | 2/2014 | Yoshimura et al. |
| 2014/0078229 A1 | 3/2014 | Jackson et al. |
| 2014/0369895 A1 | 12/2014 | Turner et al. |
| 2015/0217068 A1 | 8/2015 | Wakalopulos |
| 2015/0367013 A1 | 12/2015 | Gruenbacher et al. |
| 2015/0367014 A1 | 12/2015 | Gruenbacher et al. |
| 2015/0367016 A1 | 12/2015 | Gruenbacher et al. |
| 2015/0367356 A1 | 12/2015 | Gruenbacher et al. |
| 2015/0367364 A1 | 12/2015 | Dodd et al. |
| 2015/0367373 A1 | 12/2015 | Dodd et al. |
| 2015/0367641 A1 | 12/2015 | Giusti |
| 2015/0368001 A1 | 12/2015 | Gruenbacher et al. |
| 2015/0373840 A1 | 12/2015 | Dodd |
| 2016/0061458 A1 | 3/2016 | Van |
| 2016/0081181 A1 | 3/2016 | Gruenbacher |
| 2016/0271639 A1 | 9/2016 | Bush et al. |
| 2016/0354799 A1 | 12/2016 | Gruenbacher et al. |
| 2016/0363339 A1 | 12/2016 | Blackley |
| 2017/0072084 A1* | 3/2017 | Gruenbacher ........ B01F 3/04085 |
| 2017/0072085 A1 | 3/2017 | Gruenbacher et al. |
| 2017/0072086 A1 | 3/2017 | Gruenbacher et al. |
| 2017/0079322 A1 | 3/2017 | Li |
| 2017/0094720 A1 | 3/2017 | Gruenbacher et al. |
| 2017/0165390 A1 | 6/2017 | Gruenbacher et al. |
| 2017/0190174 A1 | 7/2017 | Dodd |
| 2018/0043048 A1 | 2/2018 | Sidawi |
| 2018/0290157 A1* | 10/2018 | Gruenbacher ............ A61L 9/122 |
| 2018/0290158 A1* | 10/2018 | Gruenbacher ........ B41J 2/17513 |
| 2018/0290159 A1* | 10/2018 | Gruenbacher .......... B41J 29/377 |
| 2019/0070852 A1 | 3/2019 | Dodd |
| 2019/0117816 A1 | 4/2019 | Dycher |
| 2019/0117817 A1 | 4/2019 | Dycher |
| 2019/0117818 A1 | 4/2019 | Dycher |
| 2019/0351088 A1 | 11/2019 | Gruenbacher |
| 2020/0405902 A1 | 12/2020 | Gruenbacher et al. |

FOREIGN PATENT DOCUMENTS

| | | |
|---|---|---|
| CN | 1223637 | 10/2005 |
| CN | 1798585 A | 7/2006 |
| CN | 101020073 | 8/2007 |
| CN | 204072869 | 1/2015 |
| EP | 1510228 A1 | 3/2005 |
| EP | 1022063 B1 | 12/2007 |
| EP | 1894727 A3 | 10/2009 |
| EP | 2143576 | 11/2012 |
| EP | 2841208 A1 | 3/2015 |
| GB | 2410468 B | 9/2008 |
| JP | S499554 U | 1/1974 |
| JP | S5810892 Y2 | 2/1983 |
| JP | H0857030 A | 3/1996 |
| JP | H09123453 A | 5/1997 |
| JP | 2002254613 A | 9/2002 |
| JP | 2004311093 | 11/2004 |
| JP | 2005185366 | 7/2005 |
| JP | 2008168223 | 7/2005 |
| JP | 2005224503 A | 8/2005 |
| JP | 2005224504 | 8/2005 |
| JP | 2006036725 A | 2/2006 |
| JP | 2006061551 A | 3/2006 |
| JP | 2006231133 A | 9/2006 |
| JP | 2007054446 | 3/2007 |
| JP | 2008061937 | 3/2008 |
| JP | 2009100850 A | 5/2009 |
| JP | 2009213901 | 9/2009 |
| JP | 2011177246 A | 9/2011 |
| JP | 2013116308 A | 6/2013 |
| JP | 2014113536 A | 6/2014 |
| JP | 2015066388 A | 4/2015 |
| KR | 100238582 | 1/2000 |
| KR | 20130107482 A | 10/2013 |
| WO | WO0130404 A1 | 5/2001 |
| WO | 0209772 A2 | 2/2002 |
| WO | WO0232470 A1 | 4/2002 |
| WO | 2004044552 A2 | 5/2004 |
| WO | 2006004902 A1 | 1/2006 |
| WO | 2006095816 A1 | 9/2006 |
| WO | WO2007083164 A3 | 10/2007 |
| WO | WO2009064453 A1 | 5/2009 |
| WO | 2011021980 A1 | 2/2011 |
| WO | WO2014043424 A1 | 3/2014 |
| WO | WO 2015/195994 A1 | 12/2015 |
| WO | WO2015175527 A4 | 5/2016 |
| WO | WO2017215726 A1 | 12/2017 |
| WO | WO2017215727 A1 | 12/2017 |
| WO | WO2017215728 A1 | 12/2017 |

OTHER PUBLICATIONS

U.S. Appl. No. 15/936,474, filed Mar. 27, 2018, Gruenbacher, et al.
U.S. Appl. No. 15/936,477, filed Mar. 27, 2018, Gruenbacher, et al.
U.S. Appl. No. 15/939,348, filed Mar. 29, 2018, Lane, et al.
U.S. Appl. No. 16/005,781, filed Jun. 12, 2018, Gruenbacher, et al.
U.S. Appl. No. 15/936,469, filed Mar. 27, 2018, Gruenbacher, et al.
All Office Actions for P&G Case 13412L; U.S. Appl. No. 14/310,401.
All Office Actions for P&G Case 13413L; U.S. Appl. No. 14/310,285.
All Office Actions for P&G Case 13413CL; U.S. Appl. No. 14/950,214.
All Office Actions for P&G Case 13414L; U.S. Appl. No. 14/310,311.
All Office Actions for P&G Case 13415L; U.S. Appl. No. 14/310,334.
All Office Actions for P&G Case 13416L; U.S. Appl. No. 14/310,367.
All Office Actions for P&G Case 12593; U.S. Appl. No. 14/024,673.
All Office Actions for P&G Case 13267; U.S. Appl. No. 14/217,524.
All Office Actions for P&G Case 13729; U.S. Appl. No. 14/658,280.
All Office Actions for P&G Case 13412C; U.S. Appl. No. 15/231,807.
All Office Actions for P&G Case 13413CC; U.S. Appl. No. 15/376,691.
All Office Actions for P&G Case 14147; U.S. Appl. No. 14/966,231.
All Office Actions for P&G Case 14600; U.S. Appl. No. 15/358,171.
All Office Actions for P&G Case 14016; U.S. Appl. No. 14/855,653.
All Office Actions for P&G Case 14017; U.S. Appl. No. 14/855,662.
All Office Actions for P&G Case 14018; U.S. Appl. No. 14/855,677.
PCT Search Report PCT/US2018/025637; 12 Pages; dated Jun. 14, 2018.

(56) References Cited

OTHER PUBLICATIONS

All Office Actions, U.S. Appl. No. 15/936,471.
All Office Actions, U.S. Appl. No. 15/936,474.
All Office Actions, U.S. Appl. No. 15/936,477.
International Search Report and Written Opinion; Appl. No. PCT/US2018/025644, dated Jun. 4, 2018, 8 pages.
International Search Report and Written Opinion; Appl. No. PCT/US2018/025645, dated Jun. 5, 2018, 9 pages.
International Search Report and Written Opinion; Appl. No. PCT/US2018/025646; dated Jun. 4, 2018, 8 pages.
All Office Actions: U.S. Appl. No. 17/019,434.
U.S. Appl. No. 17/019,434, filed Sep. 14, 2020, Dana Paul Gruenbacher, et al.
All Office Actions; U.S. Appl. No. 15/979,510.
All Office Actions; U.S. Appl. No. 18/319,576, filed May 18, 2023.
U.S. Unpublished U.S. Appl. No. 18/319,576, filed May 18, 2023, to Dana Paul Gruenbacher et. al.
EPO Search Report and Opinion for 23212879.3 dated Feb. 28, 2024, 8 pages.

\* cited by examiner

MICROFLUIDIC DELIVERY DEVICE AND METHOD FOR DISPENSING A FLUID COMPOSITION UPWARD INTO THE AIR

FIELD

The present disclosure generally relates to microfluidic delivery devices and methods for dispensing a fluid composition into the air, and, more particularly, relates to microfluidic delivery devices and methods for delivering a fluid composition horizontally or downward into the air with the assistance of a fan to redirect the fluid composition upward into the air.

BACKGROUND

Various systems exist to deliver fluid compositions, such as perfume compositions, into the air by energized (i.e. electrically/battery powered) atomization. In addition, recent attempts have been made to deliver fluid compositions, such as perfume compositions, into the air using microfluidic delivery technology such as thermal and piezo inkjet heads.

When using microfluidic delivery technology to deliver fluid compositions, especially when delivering the fluid compositions into the air, proper dispersion of the atomized fluid composition into the surrounding space may be important for consumer noticeably. Moreover, minimizing deposition of the fluid composition on nearby surfaces may also be important.

Some atomizing devices are configured to dispense a fluid composition downward. Such devices may be configured to dispense the fluid composition in a downward or horizontal direction due to requirements on the placement of the microfluidic element. Atomizing a fluid composition into the air in a downward direction can contribute to deposition of the fluid composition on the device itself or on nearby surfaces. Moreover, atomizing a fluid composition downward may not sufficiently disperse the fluid composition in the room or space to provide acceptable consumer noticeability.

As a result, it would be beneficial to provide a device that is capable of dispensing a fluid composition downward or in a horizontal direction into the air and dispersing the fluid composition throughout a room or space. Moreover, it would be beneficial to provide a device that is capable dispensing a fluid composition into the air while minimizing deposition of the fluid composition on nearby surfaces.

SUMMARY

"Combinations:"
A. A microfluidic delivery device comprising:
  a housing electrically connectable with a power source;
  a cartridge releasably connectable with the housing, wherein the cartridge comprises a reservoir for containing a fluid composition and microfluidic die in fluid communication with the reservoir, wherein the reservoir comprises a top surface, a bottom surface opposing the top surface, and a sidewall that joins the top and bottom surfaces, wherein the microfluidic die is configured to dispense substantially all of the fluid composition in a horizontal direction or a downward direction relative to horizontal, wherein horizontal is normal to the direction of gravitational force; and
  a fan connected with the housing, wherein the fan is configured to generate air flow that converges with and redirects the fluid composition dispensed from the microfluidic die in an upward direction relative to horizontal.
B. The microfluidic delivery device according to Paragraph A, wherein the microfluidic die is disposed on the bottom surface or the sidewall of the reservoir.
C. The microfluidic delivery device according to any of Paragraphs A through B further comprising an air flow channel extending from the fan to an air outlet of the housing, wherein the air flow channel comprises a first region disposed adjacent to the fan, a second region disposed adjacent to the air outlet, and a third region joining the first and second regions, wherein at least the second region is angled upward to the air outlet, relative to horizontal.
D. The microfluidic delivery device according to Paragraph C, wherein the fluid composition exiting the microfluidic die converges with air flow exiting the air outlet
E. The microfluidic delivery device according to Paragraph C, wherein the microfluidic die is disposed on the bottom surface of the reservoir, and wherein the fluid composition exiting the microfluidic die is dispensed into the air flow channel.
F. The microfluidic delivery device according to Paragraph C or E, wherein the air flow channel comprises an upper surface and a lower surface, wherein the upper surface comprises a baffle and a fluid composition outlet disposed adjacent to the baffle, wherein the baffle is disposed upstream of the fluid composition outlet and projects into the air flow channel.
G. The microfluidic delivery device according to any of Paragraphs C through F, wherein the air flow channel comprises a screen.
H. The microfluidic delivery device according to any of Paragraphs A through G, wherein the cartridge comprises a sponge.
I. The microfluidic delivery device according to any of Paragraphs A through H wherein the fluid composition comprises perfume.
J. The microfluidic delivery device according to any of Paragraphs A through I, wherein the microfluidic die comprises a piezoelectric crystal or a heater.
K. A method of dispensing a fluid composition with a microfluidic device, the method comprising the steps of:
  dispensing a fluid composition from a microfluidic delivery device into the air in a horizontal direction or downward direction relative to horizontal;
  directing air flow from a fan toward the fluid composition; and
  converging the air flow with the jetted fluid composition to redirect the fluid composition upward relative to horizontal, wherein the air flow is travelling with greater momentum than the fluid composition at the point that the air flow and the fluid composition converge.
L. The method according to Paragraph K, wherein the fluid composition comprises perfume.
M. The method according to Paragraphs K or L, wherein the microfluidic delivery device comprises microfluidic die comprising a piezoelectric crystal or a heater.
N. The method according to any of Paragraphs K through M, wherein the microfluidic delivery device comprises a housing, a cartridge that is releasably connectable with the housing, and a fan.

O. The method according to any of Paragraphs K through N, wherein the microfluidic delivery device further comprises an air flow channel extending from the fan to an air outlet of the housing, wherein the air flow channel comprises a first region disposed adjacent to the fan, a second region disposed adjacent to the air outlet, and a third region joining the first and second regions, wherein at least the second region is angled upward to the air outlet, relative to horizontal.

DETAILED DESCRIPTION

Figure 1:
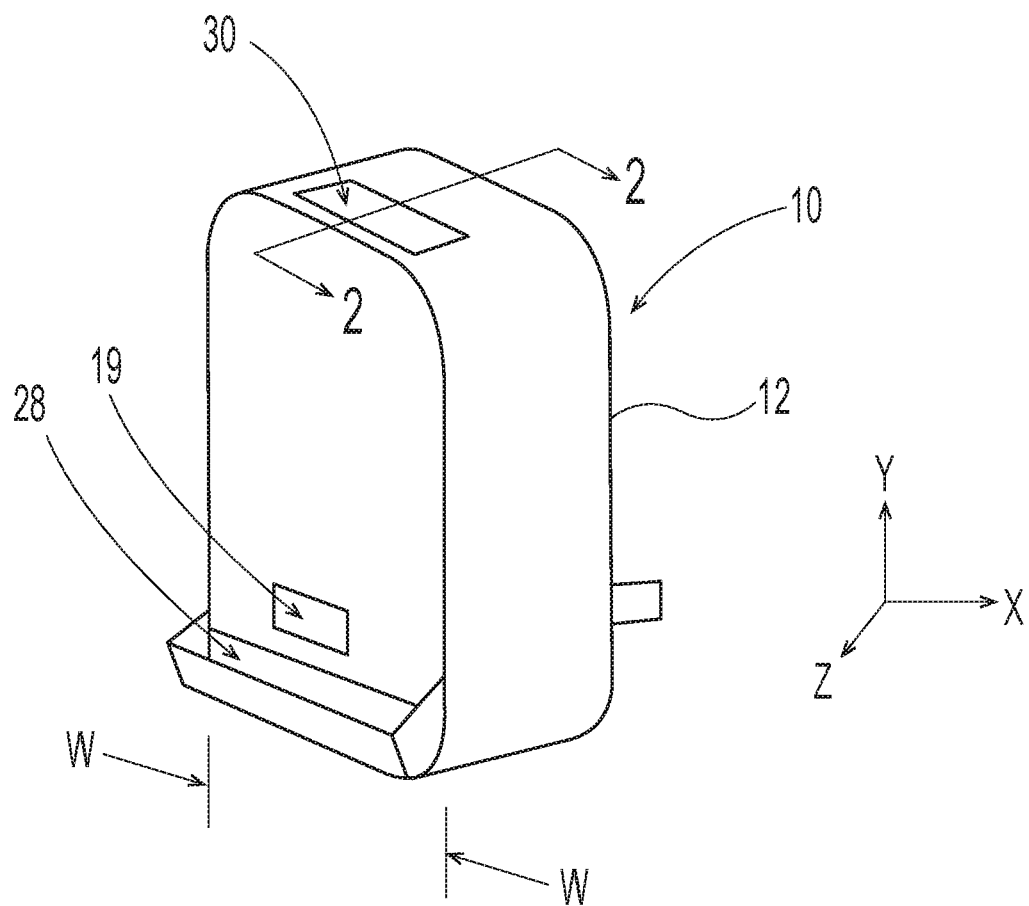
FIG. 1 is a schematic of a top, perspective view of a microfluidic delivery device.

The present disclosure includes a microfluidic delivery device comprising a cartridge having a microfluidic delivery member and methods for delivering fluid compositions upward into the air. The fluid compositions may include various components, including, for example, freshening compositions, malodor reducing compositions, perfume mixtures, and combinations thereof.

The fluid composition may travel in a substantially downward or horizontal direction out of the microfluidic die due to requirements in the placement of the microfluidic die. Microfluidic delivery devices can be vulnerable to the introduction of air into the microfluidic passages, which may render the microfluidic die inoperable. Placement of the microfluidic die substantially below the fluid reservoir or to the side of the fluid reservoir and connecting passages disposed between the reservoir and the microfluidic die may allow air to accumulate in the passages in such a way that the air does not come in contact with the microfluidic die. Conversely, a microfluidic die disposed above said passages (in order to dispense the fluid composition in a substantially upward direction) may come into contact with air bubbles which rise due to buoyancy. Air bubbles may be present in the fluid composition due to dissolution of air in the fluid composition, or through imperfect filling of the microfluidic delivery device.

The microfluidic delivery device of the present disclosure overcomes challenges associated with dispensing a fluid composition in a horizontal direction or downward direction relative to horizontal. The microfluidic delivery device may include a housing electrically connectable with a power source, a cartridge releasably connectable with the housing, and a fan connected with the housing. The cartridge has a reservoir for containing a fluid composition and a microfluidic die in fluid communication with the reservoir. The reservoir comprises a top surface, a bottom surface opposing the top surface, and a sidewall that joins the top and bottom surfaces. The die is configured such that substantially all of the fluid composition exits the microfluidic die in a horizontal direction or downward direction relative to horizontal. The fan is configured to generate air flow that converges with and redirects the fluid composition dispensed from the microfluidic die in an upward direction relative to horizontal. In order to redirect the fluid composition upward, the momentum of the air flow may be greater than the momentum of the fluid composition dispensed from the die at the point where the air flow and the fluid composition converge.

The microfluidic delivery device may include an air flow channel extending from the fan to an air outlet of the housing. The air flow channel comprises a first region disposed adjacent to the fan, a second region disposed adjacent to the air outlet, and a third region joining the first and second regions. The second region may be angled upward to the air outlet, relative to horizontal, in order to direct the air flow in a generally upward direction relative to horizontal.

A method of dispensing a fluid composition into the air may include providing a microfluidic delivery device of the present disclosure. The microfluidic delivery device may be plugged into a wall outlet such as an electric source. If plugged into the electrical outlet disposed in a wall, the wall and the outlet may be disposed on a vertical plane. The fluid composition may be jetted from the cartridge into the air in a horizontal direction or downward direction relative to horizontal. The air flow may be directed toward the fluid composition. The air flow may converge with the jetted fluid composition to redirect the fluid composition upward relative to horizontal. The air flow may be travelling with greater momentum than the fluid composition at the point where the air flow and the fluid composition converge in order to change the direction of flow of the fluid composition.

A method of dispensing a fluid composition into the air may include providing a microfluidic delivery device of the present disclosure. The microfluidic delivery device may be powered by a battery or cord such that the microfluidic delivery device rests on a surface. The surface may be disposed on a horizontal plane. The fluid composition may be jetted from the cartridge into the air in a horizontal direction or downward direction relative to horizontal. The horizontal direction may be parallel with the horizontal plane that the microfluidic delivery device rests upon. The air flow may be directed toward the fluid composition. The air flow may converge with the jetted fluid composition to redirect the fluid composition upward relative to horizontal. The air flow may be travelling with greater momentum than the fluid composition at the point where the air flow and the fluid composition converge in order to change the direction of flow of the fluid composition.

While the below description describes the microfluidic delivery device comprising a housing, a cartridge, and a fan, each having various components, it is to be understood that the microfluidic delivery device is not limited to the construction and arrangement set forth in the following description or illustrated in the drawings. The microfluidic delivery device, cartridge, and fan, of the present disclosure are applicable to other configurations or may be practiced or carried out in various ways. For example, the components of the housing may be located on the cartridge and vice-versa. Further, the housing and cartridge may be configured as a single unit versus constructing a cartridge that is separable and or replaceable from the housing as described in the following description. Moreover, the cartridge may be used with various devices for delivering fluid composition into the air.

While the present disclosure discusses the use of the microfluidic delivery devices 10 such as thermal or piezo ink-jet print head type systems, it is to be appreciated that the aspects of the present disclosure are also combinable with other fluid droplet atomizing devices, such as ultrasonic piezo systems with a plurality of nozzles and ultrasonic bath atomizers, and the like. For example, the fan and air flow channel of the present disclosure may be used with other atomizing devices to redirect the atomized fluid composition from travelling in a first direction to a second direction.

Microfluidic Delivery Device

With reference to FIGS. 1-8, the microfluidic delivery device 10 may include a housing 12, a cartridge 26 that may be releasably connectable with the housing 12, and a fan 32. The microfluidic delivery device 10 may be comprised of an upper portion 14, a lower portion 16, and a body portion 18 that extends between and connects the upper portion 14 and the lower portion 16.

The microfluidic delivery device may be configured to plug directly into a wall outlet such that the body portion 14 is adjacent to a vertical wall. Or, the microfluidic delivery device may be configured with a power cord or battery such that the lower portion 16 of the microfluidic delivery device rests on a horizontal surface, such as a table, countertop, desktop, appliance, or the like.

The housing 12 may be constructed from a single component or have multiple components that are connected to form the housing 12. The housing 12 may be defined by an interior 21 and an exterior 23. The housing 12 may at least partially contain and/or connect with the cartridge 26 and fan 32.

The cartridge 26 may be partially or substantially contained within the housing 12, or the cartridge 26 may be partially or substantially disposed on and/or connected with the exterior 23 of the housing. For example, with reference to FIGS. 1 and 2, the cartridge 26 may be disposed at least partially within the housing 12 and connected therewith. With reference to FIG. 3, at least a portion of the cartridge 26 may be disposed on the exterior of the housing 23 and connected therewith. The cartridge 26 may connect with the housing in various ways. For example, the cartridge may be slideably or rotatably connected with the housing 12 using various connector types. The connector may be spring-loaded, compression, snap, or various other connectors.

As will be discussed in further detail below, the cartridge may be configured in various ways. The cartridge 26 comprises a reservoir 50 for containing a fluid composition 52, a microfluidic die 92 that is in fluid communication with the reservoir 50, and electrical contacts 74 that connect with electrical contacts 48 on the housing 12 to deliver power and control signals to the microfluidic die 92. The microfluidic die 92 may be configured such that the fluid composition 52 is dispensed from the microfluidic die 92 in a substantially horizontal direction, substantially vertically downward direction, or generally downward direction, relative to horizontal. For example, with reference to FIGS. 1-4, the die 92, and specifically nozzles on the die, may be configured to dispense the fluid composition in a substantially horizontal direction as the fluid composition exits the microfluidic die 92. With reference to FIGS. 5 and 6, the fluid composition may travel in a substantially vertically downward direction out of the microfluidic die 92. In some configurations, such as shown in FIG. 9, the fluid composition may travel in a generally downward, angled direction.

As will be discussed further in the microfluidic delivery member section, and with reference to FIGS. 7 and 8, in order for the nozzles on the microfluidic die to dispense the fluid composition in a horizontal or downward direction, the die 92, and specifically the nozzle plate of the die 92, may be vertically oriented or oriented at an angle from horizontal of −90° to 0° such that the fluid composition is dispensed horizontally or downward, normal to the direction that the microfluidic die is disposed. In a configuration where the microfluidic delivery device 10 is plugged into an electrical outlet in a vertical wall, the nozzle plate of the die 92 may be vertically oriented or oriented at an angle from the wall of −90° to 0°.

With reference to FIGS. 1-2 and 5-6, the fluid composition may exit the microfluidic die 92 and travel through a fluid composition outlet 19 that is disposed adjacent to the microfluidic die 92. The fluid composition outlet 19 may be disposed in the cartridge 26 or in the housing 12. However, with reference to FIGS. 3-4, it is to be appreciated that in some configurations, the fluid composition may exit the microfluidic die 92 and travel directly into the air without passing through a fluid composition outlet.

The microfluidic delivery device 10 comprises a fan 32 to assist in redirecting the fluid composition from traveling in a generally downward or horizontal direction to travelling in a substantially upward direction relative to horizontal. By redirecting the fluid composition to travel in a substantially upward direction, the fluid composition may be better dispersed throughout a space and deposition of larger droplets on nearby surfaces may be minimized. In order to redirect the fluid composition dispensed from the die, the fluid composition may be dispensed in a first flow path and the air flow from the fan may be configured to travel in a second flow path that converges with the first flow path at a point of convergence C.

With reference to FIGS. 1-6, the fan 32 may configured to direct air through an air flow channel 34 and out an air outlet 28 in a generally upward direction. The fluid composition exiting the die 92 and the air flow generated by the fan 32 may combine either in the air flow channel 34 or after the air flow exits the air outlet 28. In either configuration, the air flow from the fan 32 converges with and redirects a fluid composition that is flowing in either a substantially horizontal, substantially downward, or substantially vertically downward direction and redirects the fluid composition to flow in a generally upward direction. In order to redirect the fluid composition, the air flow may carry momentum that is greater than the momentum of the flow of the fluid composition at the point where the air flow and the fluid composition converge, the point of convergence C.

With reference to FIGS. 1-6, the microfluidic delivery device 10 may comprise one or more air inlets 27 that are capable of accepting air from the exterior 23 of the housing 12 to be drawn into the fan 32. The air inlet(s) 27 may be positioned upstream of the fan 32 or the fan 32 may be connected with the air inlet 27. As discussed above, the microfluidic delivery device 10 may include one or more air outlets 28. The air outlet(s) 28 may be positioned downstream of the fan 32. For reference, and as used herein, air flow travels from upstream to downstream through the air flow channel 34. As will be discussed in more detail below, the fan 32 pulls air from the air inlet(s) 27 into the housing 12 and directs air through an air flow channel 34 and out the air outlet(s) 28. The air inlet(s) 27 and air outlet(s) 28 may have various different dimensions based upon the desired air flow conditions.

The fan 32 may be disposed at least partially within the interior 21 of the housing 12 or the fan 32 may be disposed at the exterior 23 of the housing 12. Various different types of fans may be used. An exemplary fan 32 includes a 5V 25×25×8 mm DC axial fan (Series 250, Type 255N from EBMPAPST), that is capable of delivering about 10 to about 50 liters of air per minute ("l/min"), or about 15 l/min to about 25 l/min in configurations without flow restrictions placed in the air flow channel, such as a turbulence-reducing screen. In configurations that do include such a flow restriction, the air flow volume may be substantially less, such as about 1 l/min to about 15 l/min, alternatively about 1 l/m to about 15, alternatively 1 l/m to 4 l/min. The average air flow velocity, at the point where the fluid composition and air flow converge, may be in the range of about 0.5 meters/second ("m/s") to about 15 m/s.

Figure 5:
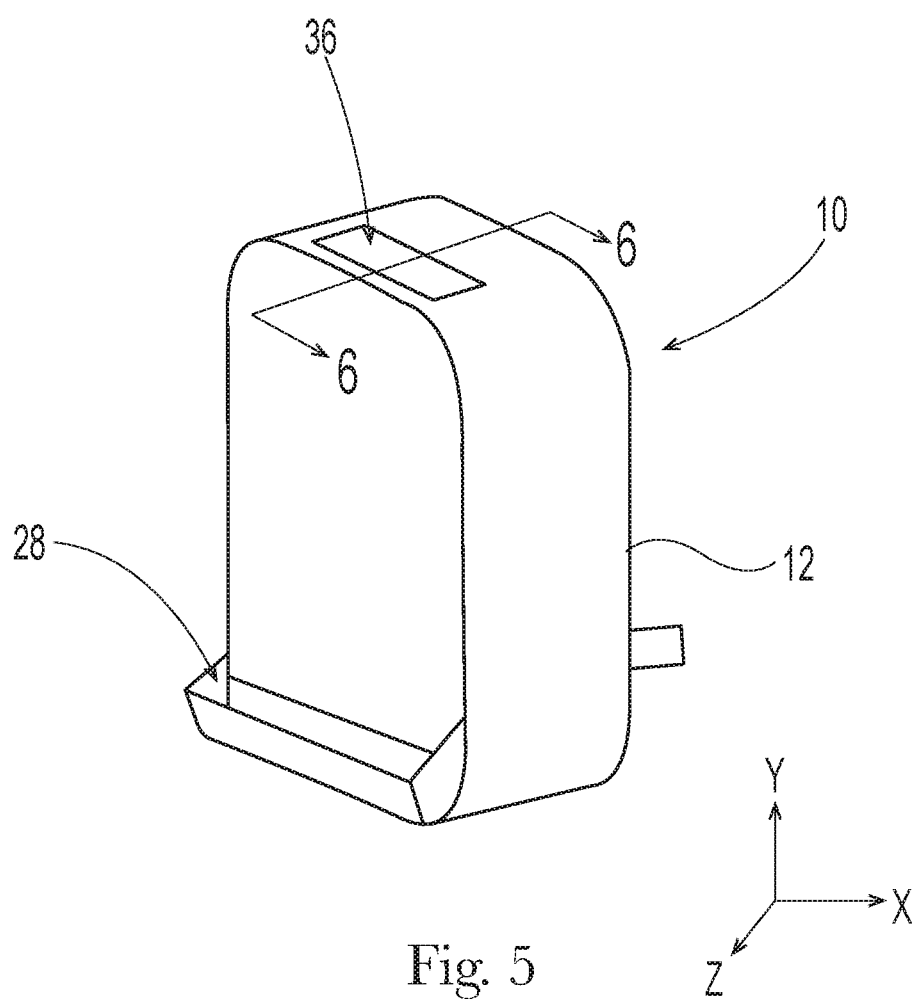
FIG. 5 is a schematic of a top, perspective view of a microfluidic delivery device.
Figure 6:
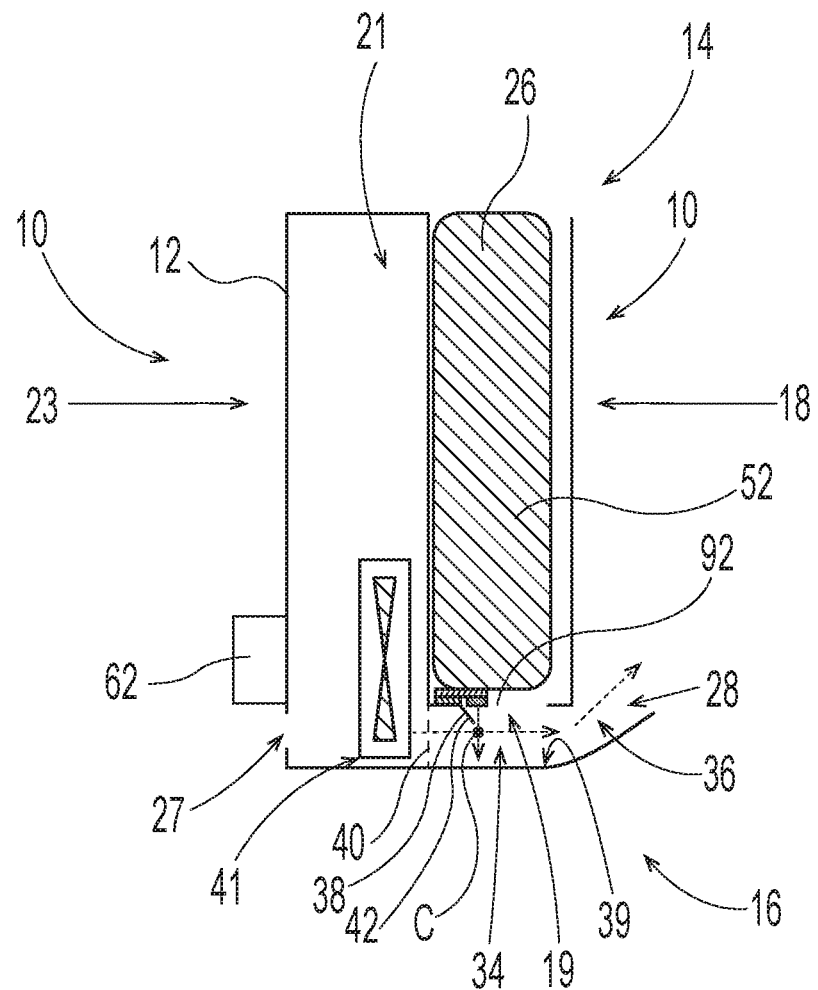
FIG. 6 is a sectional view of FIG. 1 taken along lines 6-6.

The average velocity of the air flow that converges with the fluid composition may be constrained by the dimensions of the flow channel available for changing the direction of travel of the fluid composition. In configurations where the fluid composition travels through the air flow channel 34 (such as shown in FIGS. 5-6 for illustrative purposes only), the average air flow velocity, channel dimension, and fluid composition droplet size must all be arranged such that the droplets of fluid composition enter the air flow and, through aerodynamic drag, simultaneously decelerate and change direction to follow the air flow in the air flow channel 34. For example, if the average air flow velocity is too high within the air flow channel 34, the fluid composition exiting the microfluidic die 92 will be turned parallel to the flow in the air flow channel 34 such that the fluid composition travels very close or adjacent to the surfaces of the air flow channel. In this case, even small turbulent eddies may cause the drops to collide with and deposit on the surfaces of the air flow channel. For a configuration such as shown in FIG. 5-6 for example, the air flow rate may be selected through some combination of empirical observation or mathematically modeling of the aerodynamic behavior of droplets traveling in a crossflow. As used herein, the "average velocity" of the air flow is an average of the velocities across the entire air flow stream since the air flow stream will have lower velocities near the surfaces of the air flow channel and higher velocities in the center of the air flow stream. Likewise, the "average momentum" as used herein is an average of the momentum across the entire air flow stream.

Momentum is a three-dimensional vector stating the object's momentum in the three directions of three-dimensional space. Momentum is a function of the mass of an object and the velocity of an object, according to the following equation:

$$p=mv,$$

where v is the three-dimensional velocity vector giving the object's rate of movement in each direction and m is the object's mass. Momentum is a vector that gives direction and magnitude of both fluid composition droplets $m_d \vec{v}_d$ and air flow $m_a \vec{v}_a$. As long as the momentum of the fluid composition droplets and the air flow are not in the same direction, the fluid composition direction can be changed. The degree of the fluid composition directional change caused by the air flow is dependent on momentum magnitude and angle between the air flow and flow composition. If the vertical component of air flow momentum is higher than that of the fluid composition momentum and in an upward direct, the fluid composition direction will be changed and moved upward.

In order to push the fluid composition in an upward direction, the lifting drag force $F_d$ of the air flow should be larger than droplet's gravitational force $F_g$. For horizontally dispensing the fluid composition, the lifting drag force of the air is defined by the following equation:

$$F_d = 6\pi \mu u_a \sin(\theta) a_d,$$

Where, $a_d$ is the droplet radius; $\theta$ is the outlet air flow angle relative to the horizontal direction; $\mu$ is the air viscosity that creates the drag force; $u_a$ is the magnitude of air flow velocity; $\rho_d$ is fluid composition density; $\rho_a$ is air density. For dispensing vertically downward, the lifting drag force of the air is defined by the following equation:

$$F_d = 6\pi \mu (u_a \sin(\theta) - u_d) a_d,$$

where $u_d$ is the droplet downward velocity.

If the fluid composition is dispensed at an arbitrary angle of $\varphi$ from the vertical down direction, the lifting drag force of the air is defined by the following equation:

$$F_d = 6\pi \mu (u_a \sin(\theta) - u_d \cos(\varphi)) a_d.$$

The droplet's gravitational force is defined by the following equation:

$$F_g = 4/3 \pi (\rho_d - \rho_a) a^3$$

If $F_d > F_g$, the fluid composition can flow upward.

In one exemplary configuration, the fluid composition may be dispensed downward as droplets with a volume 8 pL at an average velocity of 6 meters per second ("m/s"), with the air flow channel having a cross-sectional area of about 80 mm$^2$, and an average air flow velocity in the range of about 1.0 m/s to about 4.0 m/s.

In configurations where the fluid composition is directed horizontally and the angle through which the direction of travel must change is small (e.g., on the order of 20-45 degrees), the air flow average velocity may be much higher (e.g., on the order of 5-15 m/s). In this configuration, such as shown in FIGS. 1-4 and 9 for illustration only, the droplets travel within a very short channel, or may travel exclusively external to the dispenser, so deposition on the walls of the air flow channel is not a concern. The air flow velocity in this configuration may be specified to be a higher velocity to maximize the dispersion of droplets within the surroundings, since deposition within the dispenser does not impose a constraint on the upper limit of velocity.

As shown in FIGS. 1-6, the air flow channel 34 may be disposed in the lower or body portions 16 or 18 of the microfluidic delivery device 10. The air flow channel 34 may be disposed beneath the die 92 when the microfluidic delivery device is resting on a surface or plugged into an electrical outlet. The air flow channel 34 may be formed between at least two surfaces of the microfluidic delivery device and may extend from the fan 32 to the air outlet 28. The surfaces that form the air flow channel 34 may completely or substantially enclose the air flow channel 34 except for the fan 32 and the air outlet 28. The air flow channel 34 may be formed from at least an upper surface 38 of the microfluidic delivery device 10 and a lower surface 39 of the microfluidic delivery device 10. The upper surface and/or lower surface of the housing may be a part of the housing 12 or cartridge 26 or both. While the device and particularly the air flow channel 34 are illustrated as shown in FIGS. 1-6, it is appreciated that the air flow channel 34 and the surfaces that form the air flow channel 34 may be configured in various different ways in order to adjust the flow path, average velocity, turbulence, and any other parameters of the air flow while ultimately delivering an air flow that is capable of redirecting a fluid composition in a generally upward direction.

The air flow channel 34 may have a first region 35 that is disposed adjacent to the fan 32, a second region 36 that is disposed adjacent to the air outlet 28, and a third region 37 extending between the first and second end regions 35 and 36. At least the second region 36 of the air flow channel 34 is angled upward toward the air outlet 28 and relative to horizontal. The angled portion of the air flow channel 34 may form an angle θ from horizontal, from the viewpoint at the exterior of the cartridge. The angle θ of the second region 36 of the air flow channel relative to horizontal is shown for purposes of illustration in FIG. 4. The third region 37 and/or the first region 35 may also be angled upward. The upper surface 38 and/or lower surface 39 may be angled upward toward the air outlet 28 in order to angle the air flow channel 34 upward in at least the second region 36. As a result, air exiting the air flow channel 34 is flowing in a substantially upward direction relative to horizontal. The angle θ may be between 0° and 90°.

The configuration of the air flow channel 34 and the air outlet 28 can influence the average air velocity, average momentum and direction of the air flow. Specifically, the shape, orientation, and dimensions of the air flow channel 34 and the air outlet 28 can influence the average velocity, average momentum, and direction of the air flow obtained with the microfluidic delivery device 10. It may be desirable to limit the back pressure created in the air flow channel 34 and at the air outlet 28 in order to maximize the average velocity of the air flow that is achievable with the microfluidic delivery device. The back pressure also cause turbulence or eddies that may impede distribution of the fluid composition in the air. As a result, it may be desirable for the surfaces of the air flow channel 34 and the air outlet 28 to comprise smooth transitions and minimize sharp turns that may induce turbulence or eddies in the air flow. As discussed above, the air flow channel 34, the air outlet 28, and the fan 32 may be designed to produce an average air flow momentum that is greater than the momentum of the fluid composition at the time the air flow and fluid composition converge in order to change the direction of the fluid composition.

Figure 2:
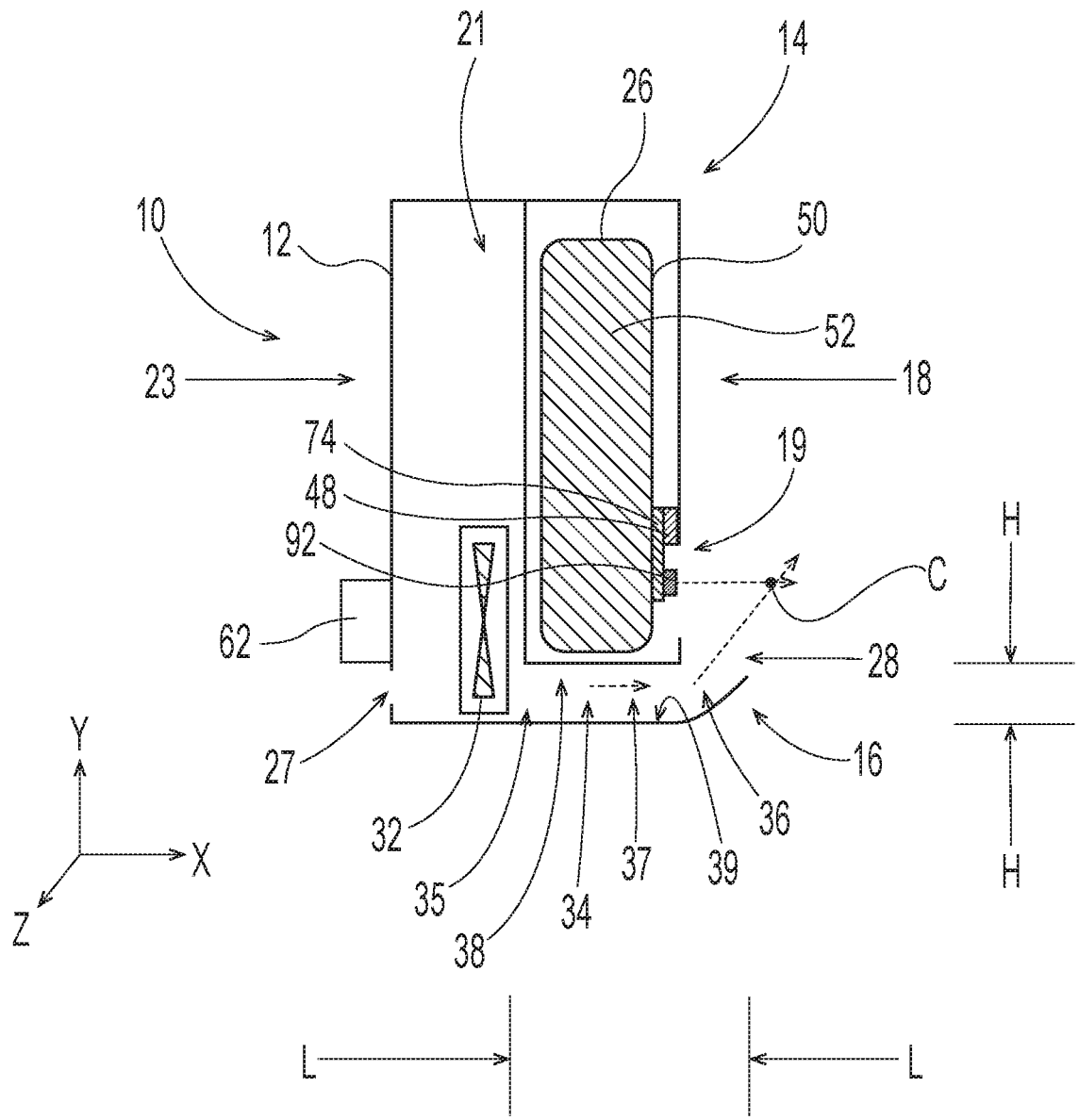
FIG. 2 is a sectional view of FIG. 1 taken along lines 2-2.
Figure 3:
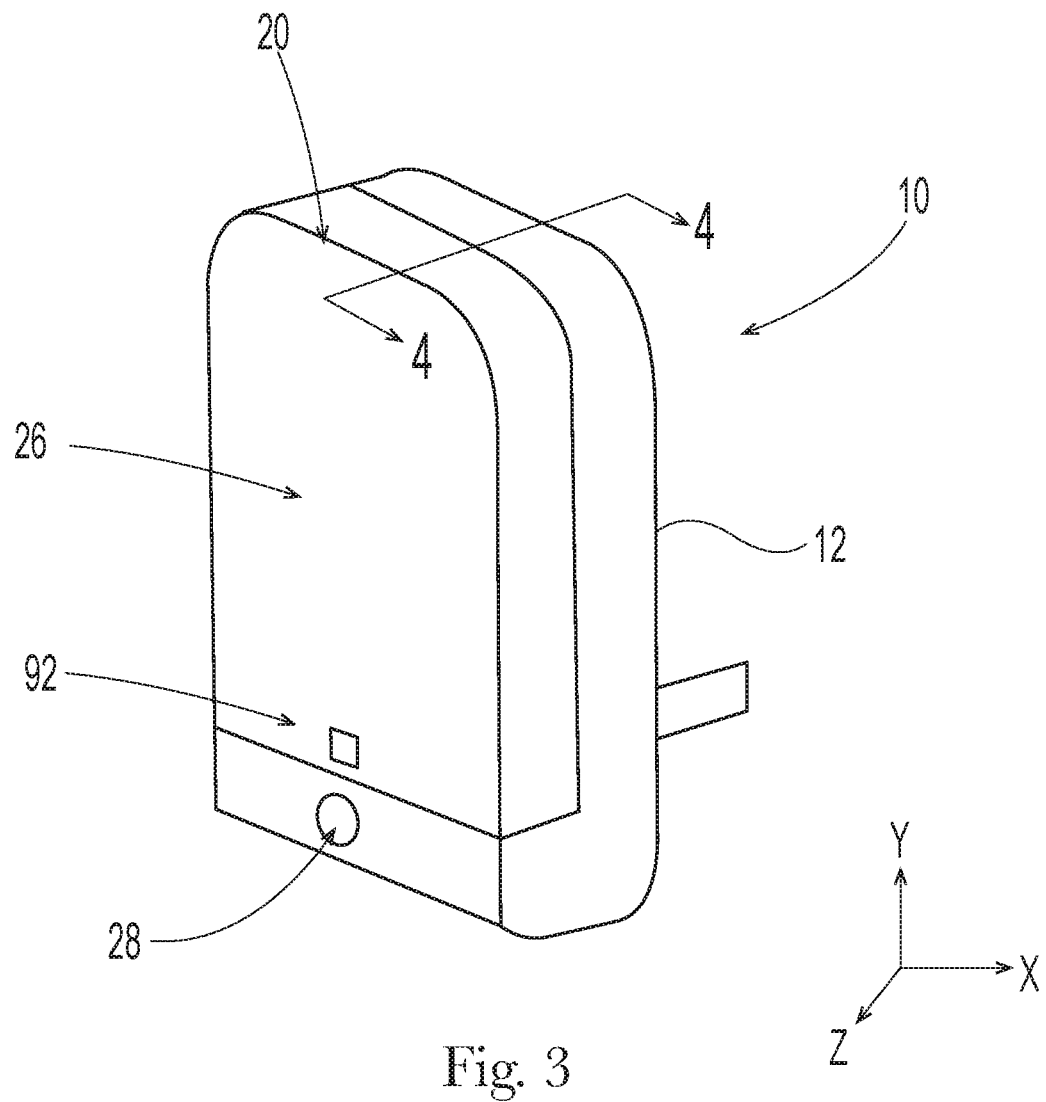
FIG. 3 is a schematic of a top, perspective view of a microfluidic delivery device.
Figure 4:
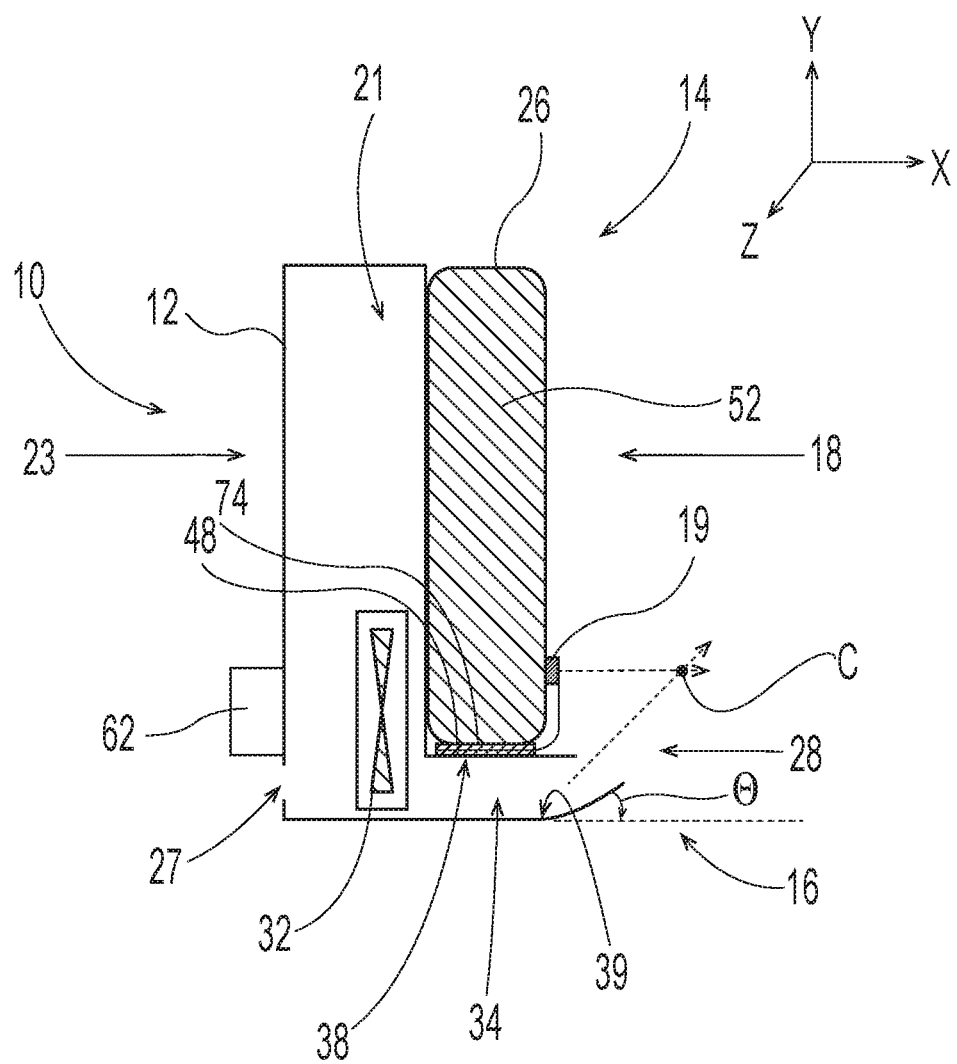
FIG. 4 is a sectional view of FIG. 1 taken along lines 4-4.

The cross-sectional area of the air outlet 28 and the orientation of the air outlet 28 can influence the impact that the air flow has on the fluid composition. In one respect, the dimensions and shape of the cross-sectional area of the air outlet 28 can influence the average air velocity and the percentage of fluid composition that is redirected by the air flow. One design consideration may be to optimize the orientation of the cross-sectional area of the air outlet 28 such that the majority of the air flow contacts the fluid composition. With reference to FIGS. 3 and 4, the air outlet 28 may have a circular shaped cross-sectional area and the cross-sectional area of the air outlet 28 may be is larger than the surface area of the die 92 to maximize the impact that the air flow has on the fluid composition. Comparing the microfluidic delivery device of FIGS. 3 and 4 with the microfluidic delivery device 10 of FIGS. 1 and 2, it is illustrated in FIGS. 1 and 2 that the cross-sectional area of the air outlet is significantly larger than the cross-sectional area of the fluid composition outlet. As a result of a design similar to the microfluidic delivery device of FIGS. 1 and 2, a large portion of the air flow will not contact the fluid composition or impact the direction of movement of the fluid composition. Whereas, the design of a microfluidic delivery device similar to FIGS. 3 and 4 will have a larger portion of the air flow contact the fluid composition. As a result of a larger portion of the air flow contacting the fluid composition, the air flow is able to have a larger impact on the directional change of the fluid composition. Stated another way, the fluid composition may be directed more vertically upward when a majority of the air flow makes direct contact with the fluid composition.

The cross-sectional area of the air outlet 28 may be configured with various different shapes. The shape of the cross-sectional area of the air outlet 28 may be round, circular, oval, tear-drop shape, triangular, square, rectangular, or any other shape. In order to maximize contact between the air flow and the fluid composition, more of the cross-sectional area should be disposed in the direction where it is desired to move the fluid. For example, as illustrated in FIGS. 1-2, more of the cross-sectional area of the air outlet 28 is disposed horizontally across the channel width W, which is away from the upward direction that the microfluidic delivery device is trying to direct the fluid composition. As a result, either a more high-powered fan may be used, or the cross-sectional area of the air outlet can be shaped to maximize the impact that the air flow has on the fluid composition. A circular (such as illustrated in FIGS. 3 and 4), vertically oriented rectangular, vertically oriented oval, or tear drop shape for the cross-sectional area of the air outlet 28 may maximize the amount of air flow that contacts the fluid composition.

Another design consideration is the angle of the air flow channel 34 at and near the air outlet 28. The larger the angle θ between the angled portion of the air flow channel and horizontal, the more vertically upward the air flow can potentially direct the fluid composition. On the other hand, the smaller or less steep of angle in the air flow channel 34, the less vertically upward the air flow can potentially direct the fluid composition. Thus, the travel path of the fluid composition after converging with the air flow is influenced by the angle of the air flow channel 34 near the air outlet 28, the shape and dimensions of the cross-sectional area of the air outlet 28

As discussed above, the air flow and fluid composition may converge after the air flow exits the air outlet 28. In such a configuration, and with reference to FIGS. 1-4, the air flow channel 34 may be positioned such that the air outlet 28 is disposed adjacent to the microfluidic die 92 and/or the fluid composition outlet 19. In such a configuration, the air flow exits the air outlet and travels in an upward direction before the air flow converges with the fluid composition dispensed from the microfluidic die 92. Upon converging, the fluid composition is redirected in a generally upward direction, relative to horizontal.

Also discussed above, the air flow and fluid composition may converge within the air flow channel 34. In particular, with reference to FIGS. 5 and 6, the microfluidic die 92 may be configured to dispense the fluid composition downward into the air flow channel 34. In such a configuration, air flow in the air flow channel 34 directs the fluid composition from the air flow channel 34 out the air outlet. When the fluid composition converges with the air flow in the air flow channel 34, the air flow may be travelling in a generally horizontal or upward direction relative to horizontal. In such a configuration, the combined stream of air flow and fluid composition exit the air outlet 28 travelling in a generally upward direction, relative to horizontal.

The channel length L, with reference to FIGS. 1 and 2, may be largely determined by the thickness of the cartridge 26, which may be from about 10 mm to about 30 mm. The channel width W may be from about 5 mm to about 50 mm. The channel height H may be governed by the aerodynamic requirements of directing the droplets through the channel 34 with minimal deposition as discussed above, and may be from about 10 mm to about 25 mm. The cross-sectional area of the air flow channel is calculated using the channel width W and the channel height H dimensions. The cross-sectional area of the air flow channel 34 may be in the range of about 40 mm$^2$ to about 150 mm$^2$, alternatively about 60 mm$^2$ to about 100 mm$^2$.

It may be desirable for the air flow to be laminar and without turbulence or eddies in order to precisely control the direction of the fluid composition into the air. This is especially useful when, for example, the fluid composition must travel in the air flow channel 34 for some distance before reaching the air outlet. Excessive turbulence or eddies may cause droplets to migrate from the center of the air flow to the surfaces of the air flow channel, thus resulting in deposition within the dispenser. Laminar flow may also improve dispersion of the fluid composition throughout a room or space. Moreover, in a configuration wherein the fluid composition is dispensed into the air flow channel 34, laminar flow may minimize deposition of the fluid composition on the surfaces of the air flow channel 34. The surfaces that form the air flow channel may be configured to maximize laminar flow throughout the entire air flow channel.

With reference to FIG. 6, the air flow channel 34 may comprise a screen 40 with one or more holes 41 for restricting the air flow. The screen 40 may encourage laminar flow, and, in turn, reduce turbulence and eddies. The screen 40 may have holes 41 which are sized to reduce the scale of turbulent eddies to a dimension much smaller than the channel height. The size of these openings may be from about 1% to about 10% of the height H of the air flow channel height 34. The screen 40 may be positioned in various locations within the air flow channel 34. While a screen is shown in the microfluidic delivery device of FIG. 6, it is to be appreciated that the microfluidic delivery device may be configured with or without the screen.

With continuing reference to FIG. 6, in a configuration where the fluid composition is dispensed into the air flow channel 34, the upper surface 38 in the first and/or third regions 35 and 37 of the air flow channel 34 may include a baffle 42 that is configured to direct the air flow away from the fluid composition outlet 19 in the housing 12. The baffle 42 may allow the fluid composition to jet downward into the air flow channel before the air flow directs the fluid composition through the air flow channel 34 and out the air outlet 28. The baffle 42 may be disposed adjacent to and upstream from the fluid composition outlet 19. The baffle 42 may project into the air flow channel 34 and/or may be angled downward toward the lower surface 39. The baffle 42 may be configured as a continuous portion of the upper surface 38 of the air flow channel 34 or as a separate component from the remaining portions of the upper surface 38. While a baffle is shown in the microfluidic delivery device of FIG. 6, it is to be appreciated that the microfluidic delivery device may be configured with or without the baffle.

With reference to FIGS. 1, 2, 5, and 6, a portion of the air flow channel 34, lower surface 39, and/or upper surface 38 may jut out horizontally beyond the adjacent body portion 18 of the microfluidic delivery device 10. Or, with reference to FIGS. 3 and 4, substantially all of the air flow channel 34, lower surface 39, and/or upper surface 38 may be substantially vertically aligned with the fluid composition outlet 19 or the microfluidic die 92 of the cartridge 26.

In a configuration where the cartridge 26 is disposed at least partially within the interior 21 of the housing, the housing may include a cover 30 such as shown in FIG. 1 for the purposes of illustration only that opens and closed to provide access to the interior of the housing 12 through an opening for inserting and removing the cartridge 26. The cover may be configured in various different ways. The cover may form a substantially air tight connection with the remainder of the housing 12 such that pressurized air in the interior 21 of the housing 12 does not escape through any gaps between the cover 30 and the housing. The housing 12 may also include opening 31 without the cover 30.

The microfluidic delivery device 10 is configured to be in electrical communication with a power source. The power source provides power to the microfluidic die 92. The electrical contacts 48 on the housing 12 connect with the electrical contacts 74 on the cartridge. The power source may be located in the interior 21 of the housing 12, such as a disposable battery or a rechargeable battery. Or, the power source may be an external power source such as an electrical outlet that connects with an electrical plug 62 connected with the housing 12. The housing 12 may include an electrical plug that is connectable with an electrical outlet. The microfluidic delivery device may be configured to be compact and easily portable. As such, the power source may include rechargeable or disposable batteries. The microfluidic delivery device may be capable for use with electrical sources as 9-volt batteries, conventional dry cells such as "A", "AA", "AAA", "C", and "D" cells, button cells, watch batteries, solar cells, as well as rechargeable batteries with recharging base. The housing 12 may include a power switch on exterior 23 of the housing 12.

Cartridge

Figures 7, 8:
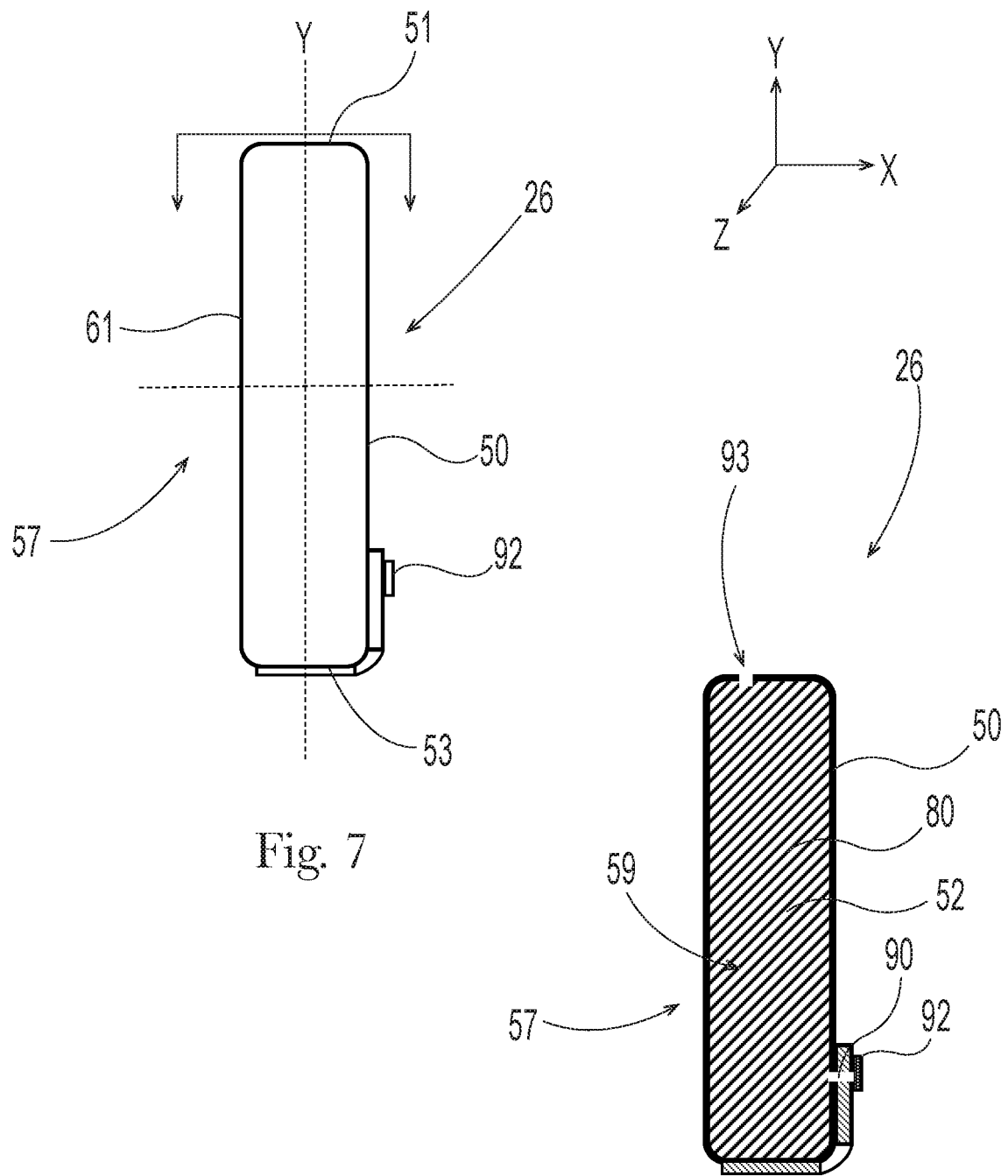
FIG. 7 is a schematic of a side, elevation view of a cartridge for a microfluidic delivery device.
FIG. 8 is a sectional view of FIG. 7 taken along lines 8-8.
Figure 9:
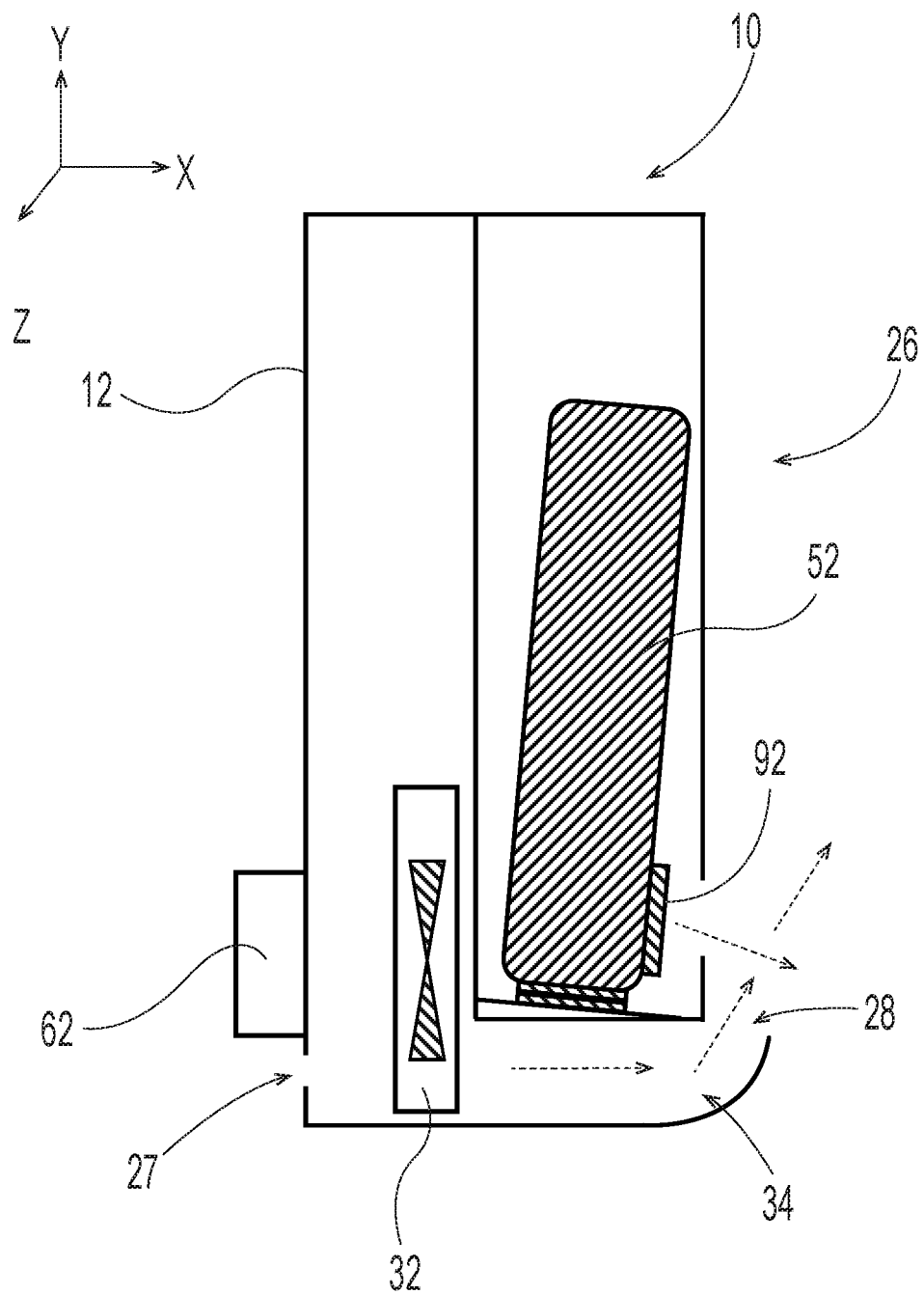
FIG. 9 is an alternative sectional view of FIG. 1 taken along lines 2-2.

As discussed above, the cartridge 26 may be configured in various different ways. With reference to FIGS. 1 and 7-8, the cartridge 26 may have a vertical axis Y and a horizontal axis X and may comprise a reservoir 50 for containing a fluid composition 52.

The reservoir 50 may be comprised of a top surface 51, a bottom surface 53 opposing the top surface 51, and at least one sidewall 61 connected with and extending between the top surface 51 and the bottom surface 53. The reservoir 50 may define an interior 59 and an exterior 57. The reservoir 50 may include an air vent 93 and a fluid outlet 90. While the reservoir 50 is shown as having a top surface 51, a bottom surface 53, and at least one sidewall 61, it is to be appreciated that the reservoir 50 may be configured in various different ways.

The reservoir 50, including the top surface 51, bottom surface 53, and sidewall(s) 61, may be configured as a single element or may be configured as separate elements that are joined together. For example, the top surface 51 or bottom surface 53 may be configured as a separate element from the remainder of the reservoir 50.

The die 92 may be disposed on the bottom surface 53 or the sidewall 61 of the reservoir 50. In either configuration, gravity and/or capillary force may assist in feeding the fluid composition 52 to the die.

The reservoir 50 may be configured to contain from about 5 milliliters (mL) to about 100 mL, alternatively from about 10 mL to about 50 mL, alternatively from about 15 mL to about 30 mL of fluid composition. The cartridge 26 may be configured to have multiple reservoirs, with each reservoir containing the same or a different fluid composition.

The reservoir can be made of any suitable material for containing a fluid composition including glass, plastic, metal, or the like. The reservoir may be transparent, translucent, or opaque or any combination thereof. For example, the reservoir may be opaque with a transparent indicator of the level of fluid composition in the reservoir.

Air Flow Channel

Figure 10:
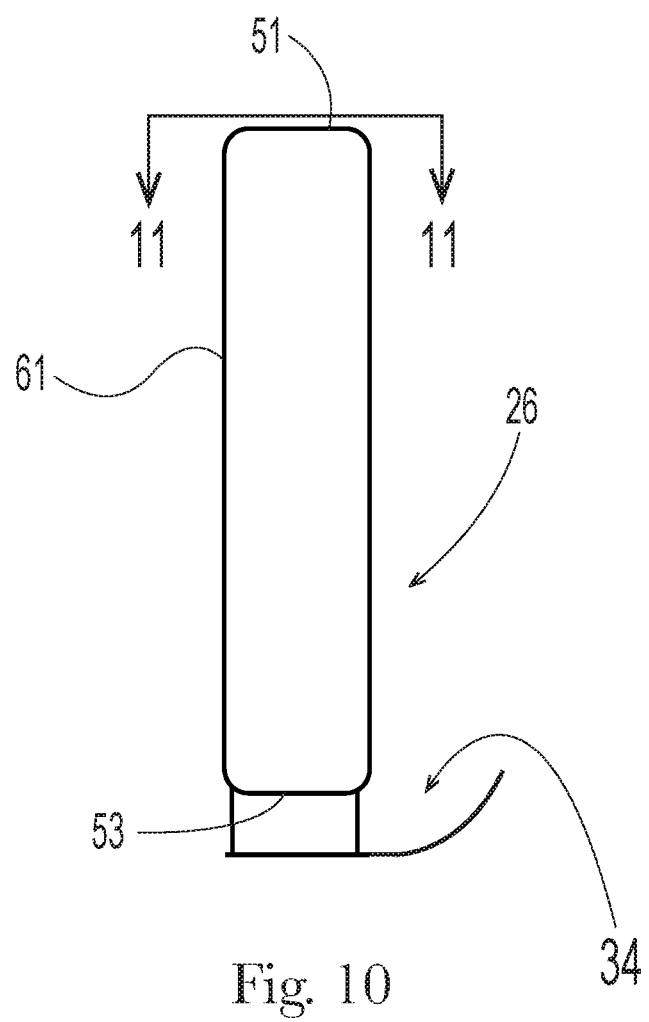
FIG. 10 is a schematic of a side, elevation view of a cartridge with an air flow channel.
Figure 11:
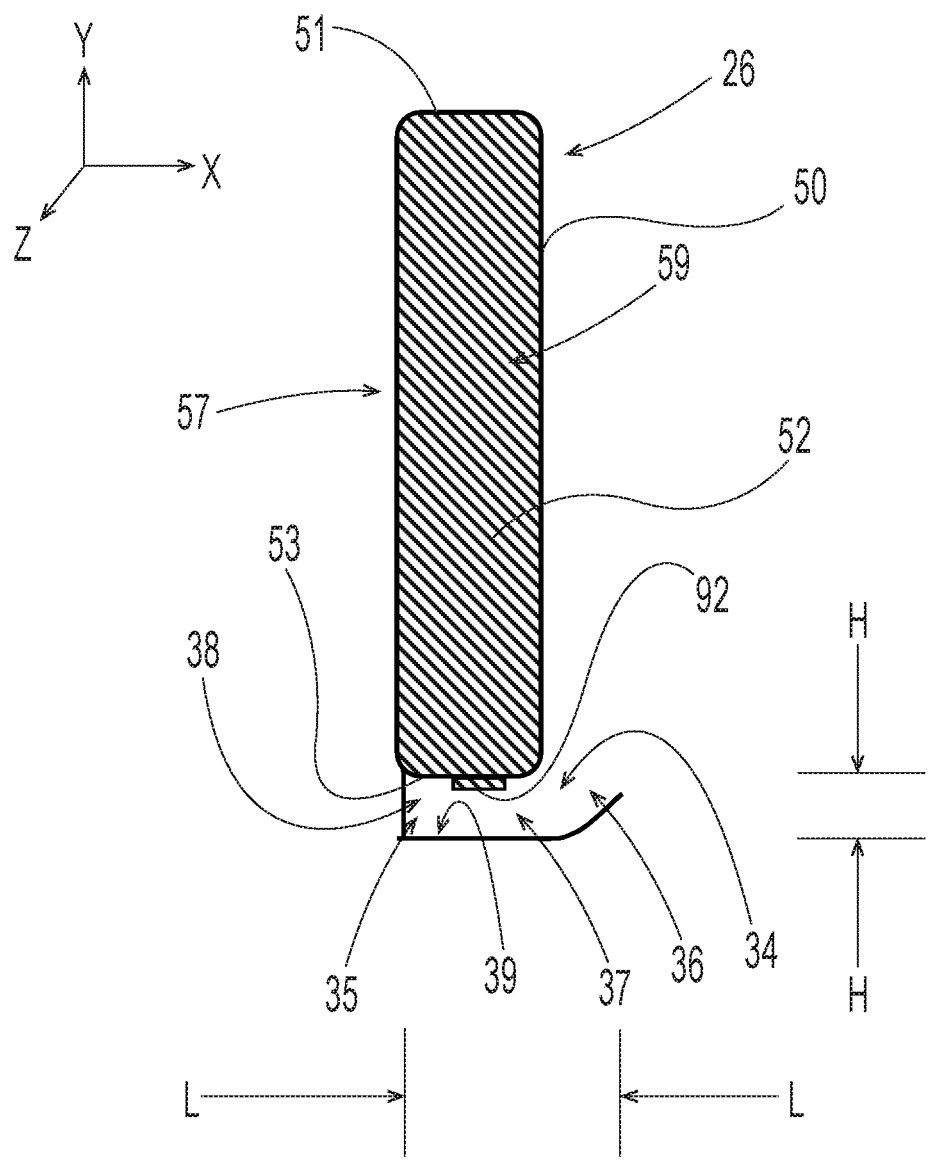
FIG. 11 is a sectional view of FIG. 10 taken along lines 11-11.

With reference to FIGS. 10 and 11, and as discussed above, the air flow channel 34 of the microfluidic delivery device 10 may be connected with and form a portion of the cartridge 26. The air flow channel 34 may adjoin the bottom surface 53 of the reservoir 50. The air flow channel 34 may be an independent component that is permanently attached with the reservoir 50 or the air flow channel 34 may be molded as a single component with the reservoir 50. For example, the upper surface 38 that forms the air flow channel 34 may be a portion of bottom surface 53 of the reservoir 50 and the lower surface 39 may be configured as a separate wall that connected therewith along a portion of the sidewall of the reservoir.

Having the air flow channel connected with the cartridge may be beneficial. For example, depending on the operating conditions, microfluidic die configuration, fluid composition details, and the like, a portion of the fluid composition may be deposited onto the surfaces that form the air flow channel. When the air flow channel is connected with a replaceable cartridge, the surfaces that form the air flow channel can be replaced with a clean air flow channel when the fluid composition is depleted form the cartridge.

Sponge

With reference to FIGS. 7 and 8, the cartridge 26 may include a sponge 80 disposed within the reservoir 50. The sponge may hold the fluid composition in the reservoir until it the die 92 is fired to eject the fluid composition. The sponge may help to create a back pressure to prevent the fluid composition from leaking from the die 92 when the die is not being fired. The fluid composition may travel through the sponge and to the die with a combination of gravity force and capillary force acting on the fluid.

The sponge may be in the form of a metal or fabric mesh, open-cell polymer foam, or fibrous or porous wick that contains multiple interconnected open cells that form fluid passages. The sponge material may be selected to be compatible with a perfume composition.

The sponge 80 can exhibit an average pore size from about 10 microns to about 500 microns, alternatively from about 50 microns to about 150 microns, alternatively about 70 microns. The average pore volume of the sponge, expressed as a fraction of the sponge not occupied by the structural composition, is from about 15% to about 85%, alternatively from about 25% to about 50%.

The average pore size of the sponge 80 and its surface properties combine to provide a capillary pressure which is balanced by the capillary pressure created by the microfluidic channels in die 92. When these pressures are in balance, the fluid composition is prevented from exiting the die 92 due to the tendency to wet the nozzle plate 132 or due to the influence of gravity.

Microfluidic Delivery Member

With reference to FIGS. 12-23, the microfluidic delivery device 10 may comprise a microfluidic delivery member 64 that utilizes aspects of ink-jet print head systems, and more particularly, aspects of thermal or piezo ink-jet print heads. The microfluidic delivery member 64 may be connected with the bottom surface 53 and/or sidewall 61 of the cartridge 26.

In a "drop-on-demand" ink-jet printing process, a fluid composition is ejected through a very small orifice of a diameter typically about 5-50 microns, or between about 10 and about 40 microns, in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. Thermal ink-jet printers employ a heating element within the print head to volatilize a portion of the composition that propels a second portion of fluid composition through the orifice nozzle to form droplets in proportion to the number of on/off cycles for the heating element. The fluid composition is forced out of the nozzle when needed. Conventional ink-jet printers are more particularly described in U.S. Pat. Nos. 3,465,350 and 3,465,351.

The microfluidic delivery member 64 may be in electrical communication with the power source of the microfluidic delivery device and may include a printed circuit board ("PCB") 106 and a microfluidic die 92 that are in fluid communication with the reservoir 50.

Figure 12:
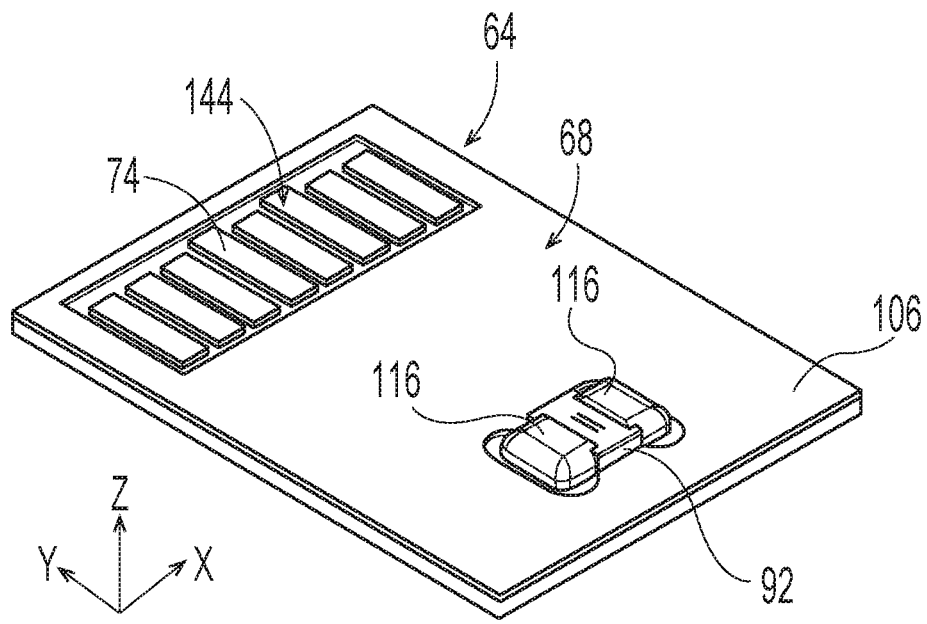
FIG. 12 is a top, perspective view of a microfluidic delivery member having a rigid PCB.
Figure 13:
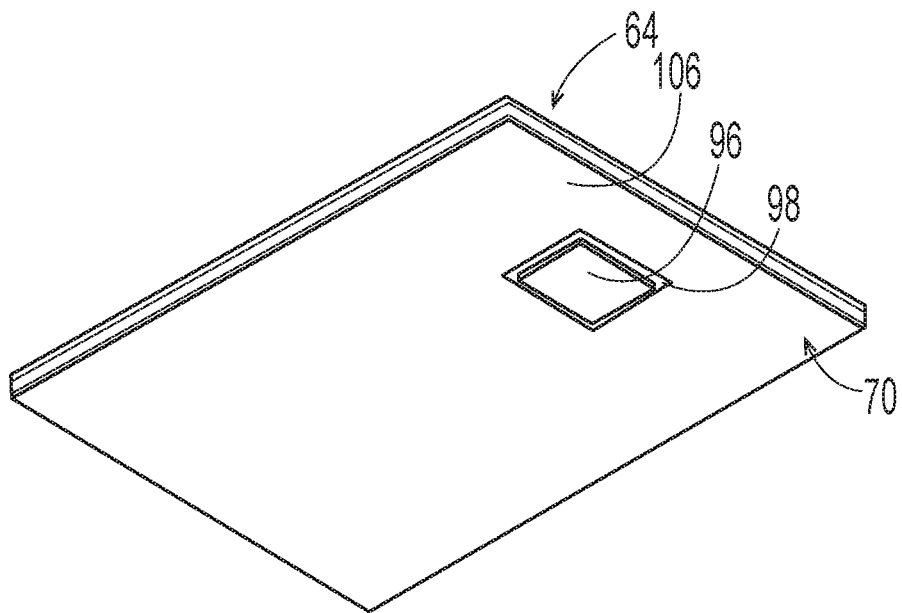
FIG. 13 is a bottom, perspective view of a microfluidic delivery member having a rigid PCB.
Figure 14:
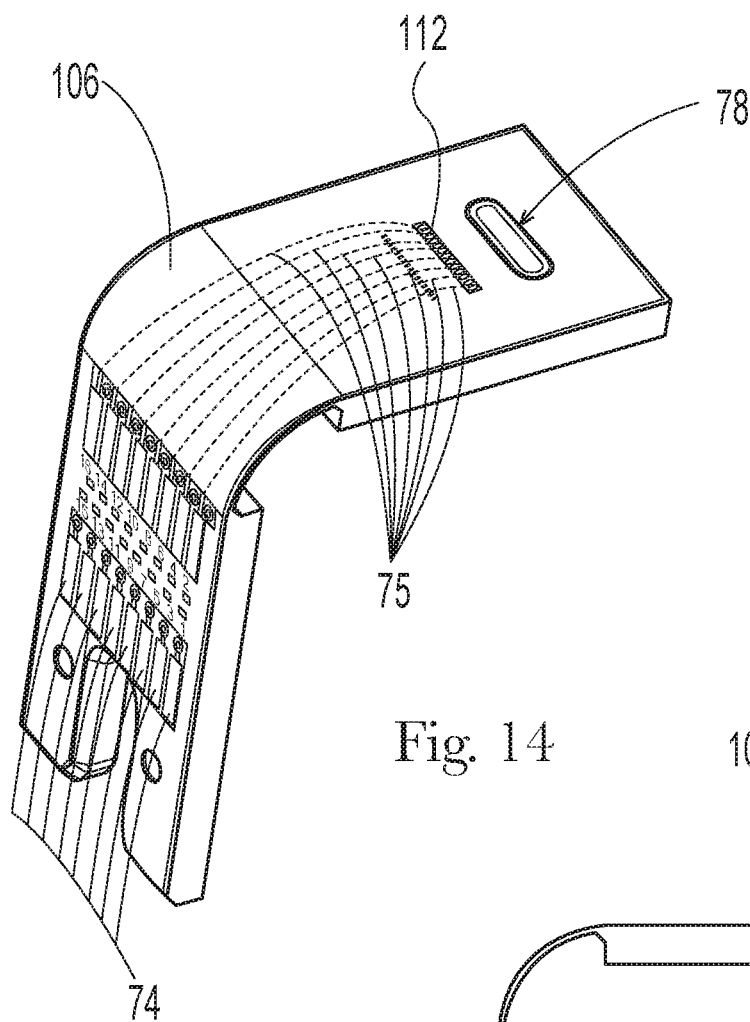
FIG. 14 is a perspective view of a semi-flex PCB for a microfluidic delivery member.
Figure 15:
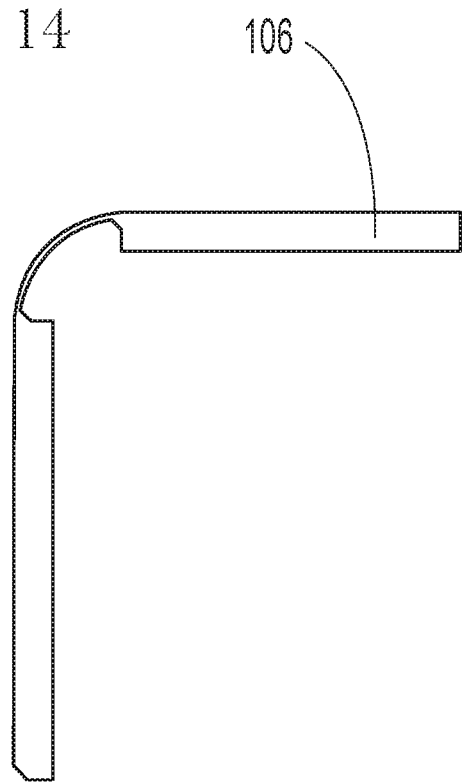
FIG. 15 is a side, elevation view of a semi-flex PCB for a microfluidic delivery member.

The PCB 106 may be a rigid planar circuit board, such as shown in FIGS. 12 and 13 for illustrative purposes only; a flexible PCB; or a semi-flex PCB, such as shown in FIGS. 14 and 15 for illustrative purposes only. The semi-flex PCB shown in FIGS. 14 and 15 may include a fiberglass-epoxy composite that is partially milled in a portion that allows a portion of the PCB 106 to bend. The milled portion may be milled to a thickness of about 0.2 millimeters. The PCB 106 has upper and lower surfaces 68 and 70.

The PCB 106 may be of a conventional construction. It may comprise a ceramic substrate. It may comprise a fiberglass-epoxy composite substrate material and layers of conductive metal, normally copper, on the top and bottom surfaces. The conductive layers are arranged into conductive paths through an etching process. The conductive paths are protected from mechanical damage and other environmental effects in most areas of the board by a photo-curable polymer layer, often referred to as a solder mask layer. In selected areas, such as the liquid flow paths and wire bond attachment pads, the conductive copper paths are protected by an inert metal layer such as gold. Other material choices could be tin, silver, or other low reactivity, high conductivity metals.

Still referring to FIGS. 12-16, the PCB 106 may include all electrical connections—the contacts 74, the traces 75, and the contact pads 112. The contacts 74 and contact pads 112 may be disposed on the same side of the PCB 106 as shown in FIGS. 12-16, or may be disposed on different sides of the PCB.

With reference to FIGS. 12 and 13, the microfluidic die 92 and the contacts 74 may be disposed on parallel planes. This allows for a simple, rigid PCB 106 construction. The contacts 74 and the microfluidic die 92 may be disposed on the same side of the PCB 106 or may be disposed on opposite sides of the PCB 106.

With continuing reference to FIGS. 12-16, the PCB 106 may include the electrical contacts 74 at the first end and contact pads 112 at the second end proximate the microfluidic die 92. FIG. 14 illustrates the electrical traces 75 that extend from the contact pads 112 to the electrical contacts and are covered by the solder mask or another dielectric layer. Electrical connections from the microfluidic die 92 to the PCB 106 may be established by a wire bonding process, where small wires, which may be composed of gold or aluminum, are thermally attached to bond pads on the silicon microfluidic die and to corresponding bond pads on the board. An encapsulant material 116, normally an epoxy compound, is applied to the wire bond area to protect the delicate connections from mechanical damage and other environmental effects.

Figure 16:
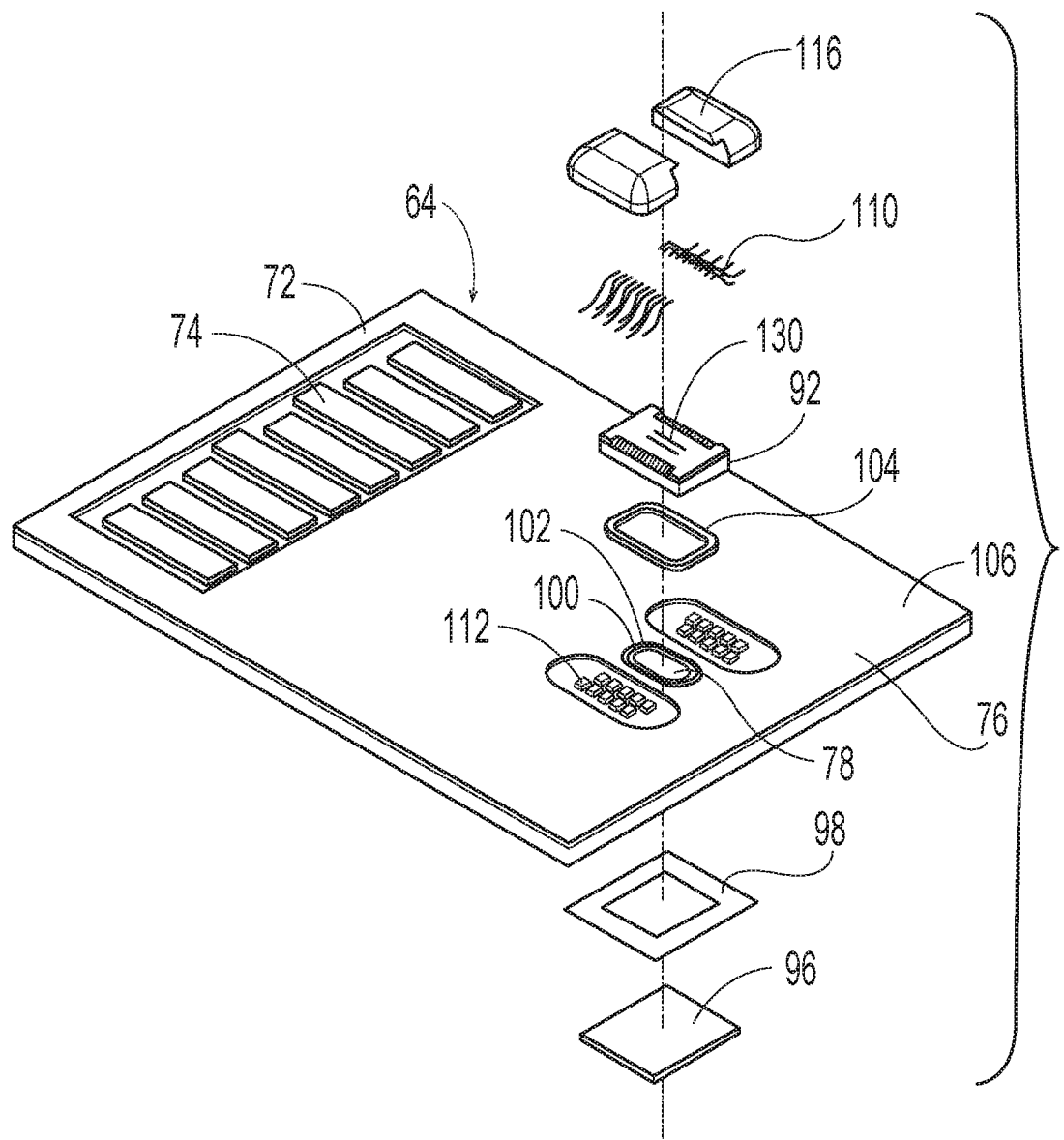
FIG. 16 is an exploded view of a microfluidic delivery member.

With reference to FIGS. 13 and 16, the microfluidic delivery member 64 may include a filter 96. The filter 96 may be disposed on the lower surface 70 of the PCB 106. The e filter 96 may be configured to prevent at least some of particulates from passing through the opening 78 to prevent clogging the nozzles 130 of the microfluidic die 92. The filter 96 may be configured to block particulates that are greater than one third of the diameter of the nozzles 130. The filter 96 may be a stainless steel mesh. The filter 96 may be randomly weaved mesh, polypropylene or silicon based.

With reference to FIGS. 13 and 16, the filter 96 may be attached to the bottom surface with an adhesive material that is not readily degraded by the fluid composition in the reservoir 50. The adhesive may be thermally or ultraviolet activated. The filter 96 is separated from the bottom surface of the microfluidic delivery member 64 by a mechanical spacer 98. The mechanical spacer 98 creates a gap between the bottom surface 70 of the microfluidic delivery member 64 and the filter 96 proximate the opening 78. The mechanical spacer 98 may be a rigid support or an adhesive that conforms to a shape between the filter 96 and the microfluidic delivery member 64. In that regard, the outlet of the filter 96 is greater than the diameter of the opening 78 and is offset therefrom so that a greater surface area of the filter 96 can filter fluid composition than would be provided if the filter was attached directly to the bottom surface 70 of the microfluidic delivery member 64 without the mechanical spacer 98. It is to be appreciated that the mechanical spacer 98 allows suitable flow rates through the filter 96. That is, as the filter 96 accumulates particles, the filter will not slow down the fluid flowing therethrough. The outlet of the filter 96 may be about 4 mm$^2$ or larger and the standoff is about 700 microns thick.

The opening 78 may be formed as an oval, as is illustrated in FIG. 16; however, other shapes are contemplated depending on the application. The oval may have the dimensions of a first diameter of about 1.5 mm and a second diameter of about 700 microns. The opening 78 exposes sidewalls 102 of the PCB 106. If the PCB 106 is an FR4 PCB, the bundles of fibers would be exposed by the opening. These sidewalls are susceptible to fluid composition and thus a liner 100 is included to cover and protect these sidewalls. If fluid composition enters the sidewalls, the PCB 106 could begin to deteriorate, cutting short the life span of this product.

Figure 18:
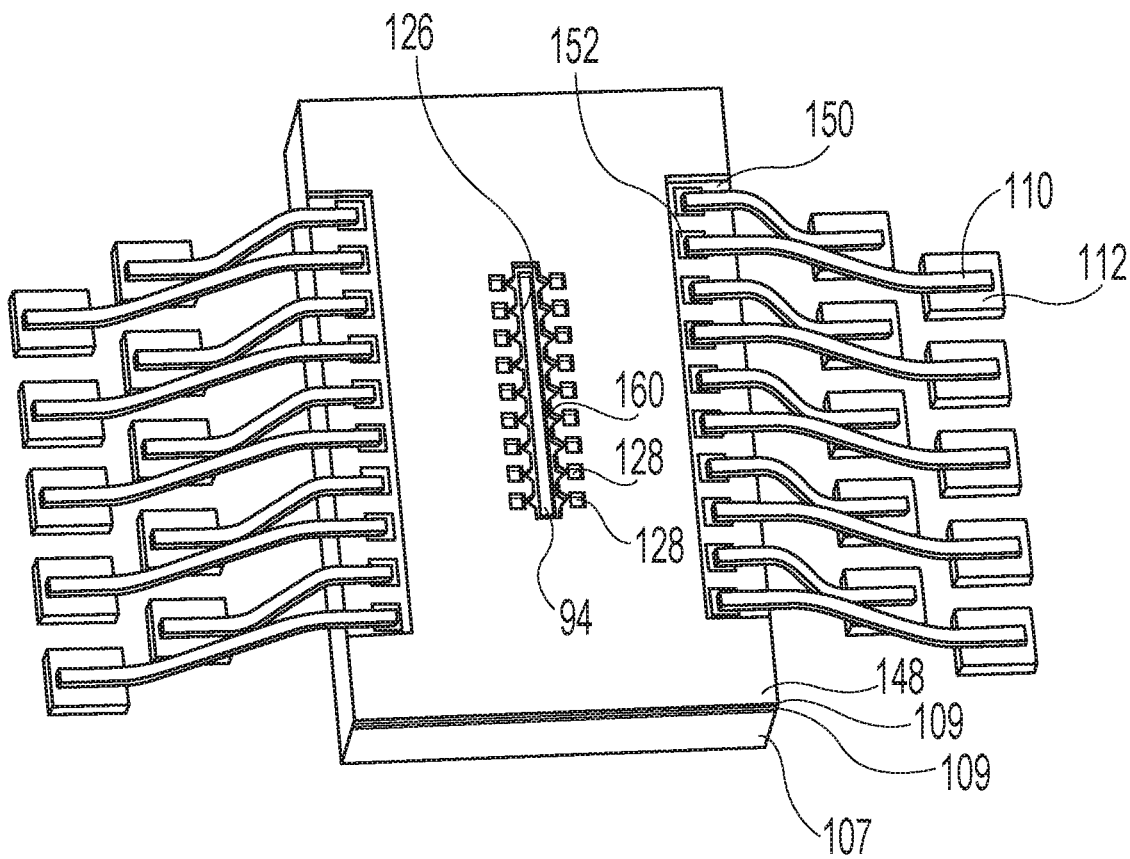
FIG. 18 is a top, perspective view of a microfluidic die with a nozzle plate removed to show fluid chambers of the die.
Figure 19:
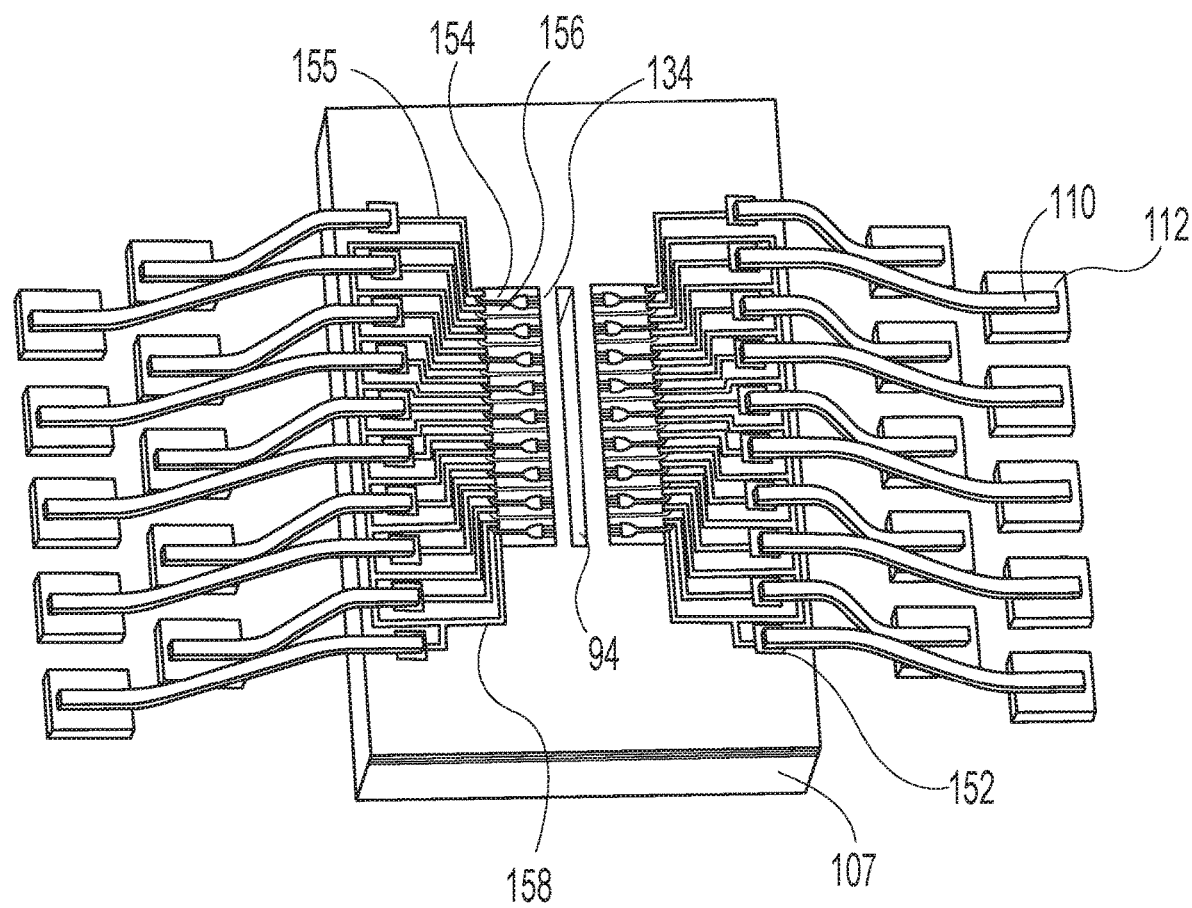
FIG. 19 is a top, perspective view of a microfluidic die with layers of the microfluidic die removed to show the dielectric layer of the die.
Figure 20:
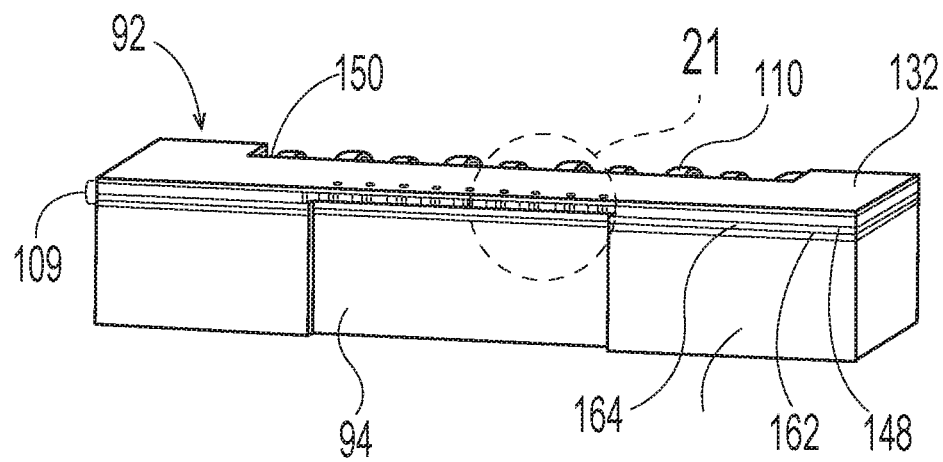
FIG. 20 is a sectional view of FIG. 17 taken along lines 20-20.
Figure 21:
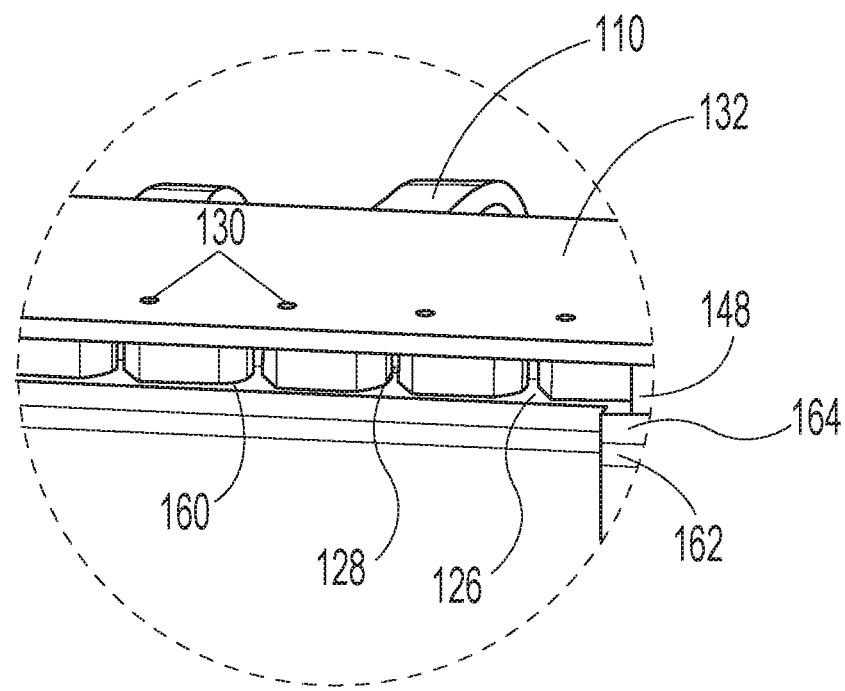
FIG. 21 is an enlarged view of portion 21 taken from FIG. 20.
Figure 22:
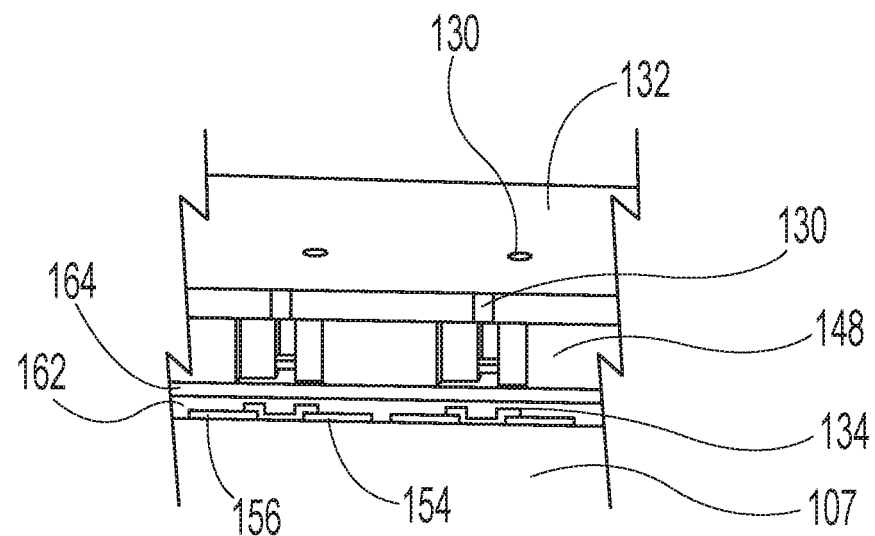
FIG. 22 is a sectional view of FIG. 17 taken along lines 22-22.

With reference to FIGS. 16-23, the PCB 106 may carry a microfluidic die 92. The microfluidic die 92 comprises a fluid injection system made by using a semiconductor micro fabrication process such as thin-film deposition, passivation, etching, spinning, sputtering, masking, epitaxy growth, wafer/wafer bonding, micro thin-film lamination, curing, dicing, etc. These processes are known in the art to make MEMs devices. The microfluidic die 92 may be made from silicon, glass, or a mixture thereof. With reference to FIGS. 20 and 21, the microfluidic die 92 comprises a plurality of microfluidic chambers 128, each comprising a corresponding actuation element: heating element or electromechanical actuator. In this way, the microfluidic die's fluid injection system may be micro thermal nucleation (e.g. heating element) or micro mechanical actuation (e.g. thin-film piezoelectric). One type of microfluidic die for the microfluidic delivery member is an integrated membrane of nozzles obtained via MEMs technology as described in U.S. 2010/0154790, assigned to STMicroelectronics S.R.I., Geneva, Switzerland. In the case of a thin-film piezo, the piezoelectric material (e.g. lead zirconinum titanate)" is typically applied via spinning and/or sputtering processes. The semiconductor micro fabrication process allows one to simultaneously make one or thousands of MEMS devices in one batch process (a batch process comprises of multiple mask layers).

With reference to FIG. 16, the microfluidic die 92 may be secured to the upper surface 68 of the PCB 106 above the opening 78. The microfluidic die 92 may be secured to the upper surface of the PCB 106 by any adhesive material configured to hold the semiconductor microfluidic die to the board.

The microfluidic die 92 may comprise a silicon substrate, conductive layers, and polymer layers. The silicon substrate forms the supporting structure for the other layers, and contains a channel for delivering fluid composition from the bottom of the microfluidic die to the upper layers. The conductive layers are deposited on the silicon substrate, forming electrical traces with high conductivity and heaters with lower conductivity. The polymer layers form passages, firing chambers, and nozzles 130 which define the drop formation geometry.

With reference to FIGS. 16-19, the microfluidic die 92 includes a substrate 107, a plurality of intermediate layers 109, and a nozzle plate 132. The nozzle plate 132 includes an outer surface 133. The plurality of intermediate layers 109 include dielectric layers and a chamber layer 148 that are positioned between the substrate and the nozzle plate 132. The nozzle plate 132 may be about 12 microns thick.

As discussed above, and with reference to FIGS. 7, 8, and 17, in order to dispense the fluid composition in a horizontal or downward direction, the die 92, and specifically the nozzle plate 132 of the die 92, may be vertically oriented or oriented at an angle from horizontal of −90° to 0°. In a configuration where the microfluidic delivery device 10 is plugged into an electrical outlet in a wall, the nozzle plate 132 of the die 92 may be vertically oriented or oriented at an angle from the wall of −90° to 0°.

Figure 17:
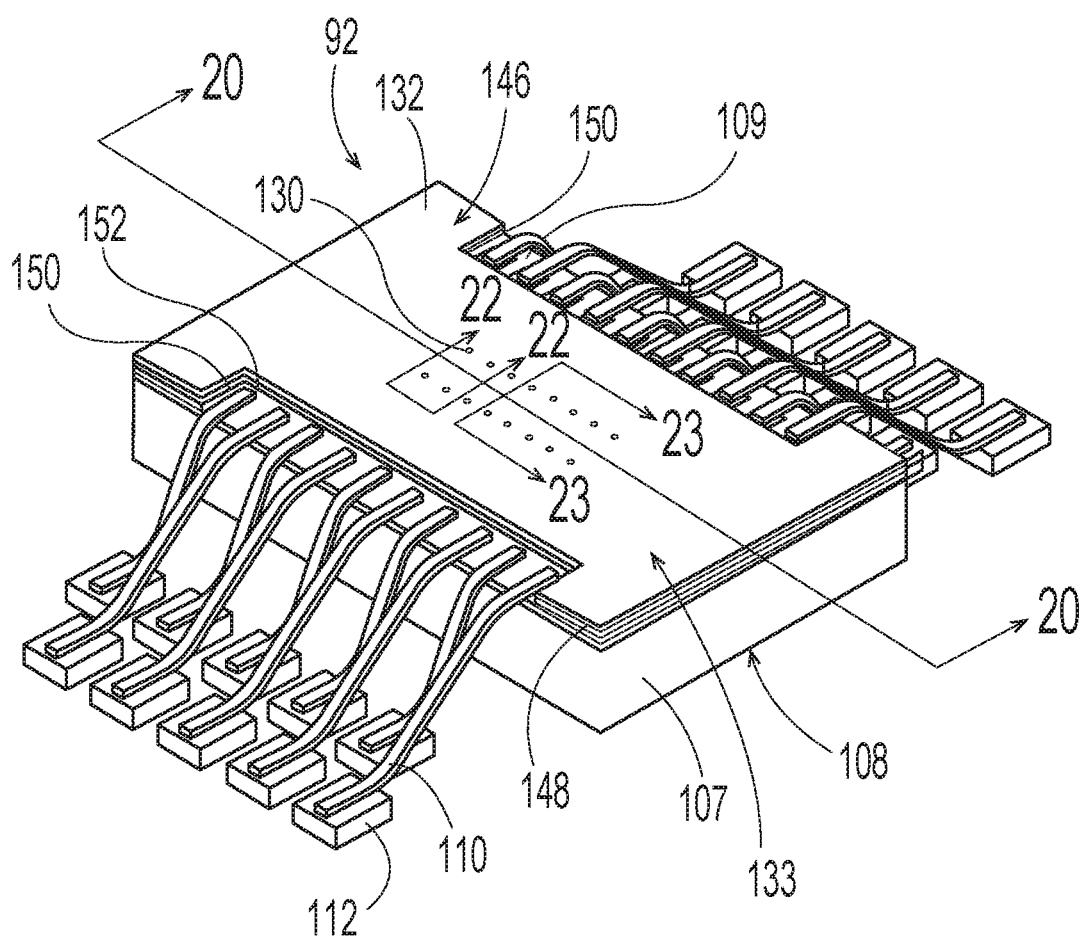
FIG. 17 is a top, perspective view of a microfluidic die of a microfluidic delivery member.

With reference to FIGS. 16-18, the microfluidic die 92 includes a plurality of electrical connection leads 110 that extend from one of the intermediate layers 109 down to the contact pads 112 on the circuit PCB 106. At least one lead couples to a single contact pad 112. Openings 150 on the left and right side of the microfluidic die 92 provide access to the intermediate layers 109 to which the connection leads 110 are coupled. The openings 150 pass through the nozzle plate 132 and chamber layer 148 to expose contact pads 152 that are formed on the intermediate dielectric layers 109. There may be one opening 150 positioned on only one side of the microfluidic die 92 such that all of the leads that extend from the microfluidic die extend from one side while other side remains unencumbered by the leads.

With reference to FIGS. 16 and 17, the nozzle plate 132 may include about 4-100 nozzles 130, or about 6-80 nozzles, or about 8-64 nozzles. For illustrative purposes only, there are eighteen nozzles 130 shown through the nozzle plate 132, nine nozzles on each side of a center line. Each nozzle 130 may deliver about 0.5 to about 20 picoliters, or about 1 to about 10 picoliters, or about 2 to about 6 picoliters of a fluid composition per electrical firing pulse. The volume of fluid composition delivered from each nozzle per electrical firing pulse may be analyzed using image-based drop analysis where strobe illumination is coordinated in time with the production of drops, one example of which is the JetXpert system, available from ImageXpert, Inc. of Nashua, NH, with the droplets measured at a distance of 1-3 mm from the top of the microfluidic die. The nozzles 130 may be positioned about 60 um to about 110 µm apart. Twenty nozzles 130 may be present in a 3 mm$^2$ area. The nozzles 130 may have a diameter of about 5 µm to about 40 µm, or 10 µm to about 30 µm, or about 20 µm to about 30 µm, or about 13 µm to about 25 µm. FIG. 18 is a top down isometric view of the microfluidic die 92 with the nozzle plate 132 removed, such that the chamber layer 148 is exposed.

Generally, the nozzles 130 are positioned along a fluidic feed channel through the microfluidic die 92 as shown in FIGS. 20 and 21. The nozzles 130 may include tapered sidewalls such that an upper opening is smaller than a lower opening. The heater may be square, having sides with a length. In one example, the upper diameter is about 13 µm to about 18 µm and the lower diameter is about 15 µm to about 20 µm. At 13 µm for the upper diameter and 18 µm for the lower diameter, this would provide an upper area of 132.67 µm and a lower area of 176.63 µm. The ratio of the lower diameter to the upper diameter would be around 1.3 to 1. In addition, the area of the heater to an area of the upper opening would be high, such as greater than 5 to 1 or greater than 14 to 1.

Each nozzle 130 is in fluid communication with the fluid composition in the reservoir 50 by a fluid path. Referring to FIGS. 8, 16, 20 and 21, the fluid path from the reservoir 50 includes through-hole 90, through the opening 78 of the PCB 106, through an inlet 94 of the microfluidic die 92, through a channel 126, and then through the chamber 128 and out of the nozzle 130 of the microfluidic die 92.

Proximate each nozzle chamber 128 is a heating element 134 (see FIGS. 19 and 22) that is electrically coupled to and activated by an electrical signal being provided by one of the contact pads 152 of the microfluidic die 92. Referring to FIG. 19, each heating element 134 is coupled to a first contact 154 and a second contact 156. The first contact 154 is coupled to a respective one of the contact pads 152 on the microfluidic die by a conductive trace 155. The second contact 156 is coupled to a ground line 158 that is shared with each of the second contacts 156 on one side of the microfluidic die. There may be only a single ground line that is shared by contacts on both sides of the microfluidic die. Although FIG. 19 is illustrated as though all of the features are on a single layer, they may be formed on several stacked layers of dielectric and conductive material. Further, while the illustrated embodiment shows a heating element 134 as the activation element, the microfluidic die 92 may comprise piezoelectric actuators in each chamber 128 to dispense the fluid composition from the microfluidic die.

In use, with reference to FIGS. 18 and 21, when the fluid composition in each of the chambers 128 is heated by the heating element 134, the fluid composition vaporizes to create a bubble. The expansion that creates the bubble causes fluid composition to eject from the nozzle 130 and to form a plume of one or more droplets.

With reference to FIGS. 17 and 18, the substrate 107 includes an inlet path 94 coupled to a channel 126 that is in fluid communication with individual chambers 128, forming part of the fluid path. Above the chambers 128 is the nozzle plate 132 that includes the plurality of nozzles 130. Each nozzle 130 is above a respective one of the chambers 128. The microfluidic die 92 may have any number of chambers and nozzles, including one chamber and nozzle. For illustrative purposes only, the microfluidic die is shown as including eighteen chambers each associated with a respective nozzle. Alternatively, it can have ten nozzles and two chambers provided fluid composition for a group of five nozzles. It is not necessary to have a one-to-one correspondence between the chambers and nozzles.

As best seen in FIG. 18, the chamber layer 148 defines angled funnel paths 160 that feed the fluid composition from the channel 126 into the chamber 128. The chamber layer 148 is positioned on top of the intermediate layers 109. The chamber layer defines the boundaries of the channels and the plurality of chambers 128 associated with each nozzle 130. The chamber layer may be formed separately in a mold and then attached to the substrate. The chamber layer may be formed by depositing, masking, and etching layers on top of the substrate.

With reference to FIGS. 18-21, the intermediate layers 109 include a first dielectric layer 162 and a second dielectric layer 164. The first and second dielectric layers are between the nozzle plate and the substrate. The first dielectric layer 162 covers the plurality of first and second contacts 154, 156 that are formed on the substrate and covers the heaters 134 associated with each chamber. The second dielectric layer 164 covers the conductive traces 155.

With reference to FIG. 19, the first and second contacts 154, 156 are formed on the substrate 107. The heaters 134 are formed to overlap with the first and second contacts 154, 156 of a respective heater assembly. The contacts 154, 156 may be formed of a first metal layer or other conductive material. The heaters 134 may be formed of a second metal layer or other conductive material. The heaters 134 are thin-film resistors that laterally connect the first and second contacts 154, 156. Instead of being formed directly on a top surface of the contacts, the heaters 134 may be coupled to the contacts 154, 156 through vias or may be formed below the contacts.

The heater 134 may be a 20-nanometer thick tantalum aluminum layer. The heater 134 may include chromium silicon films, each having different percentages of chromium and silicon and each being 10 nanometers thick. Other materials for the heaters 134 may include tantalum silicon nitride and tungsten silicon nitride. The heaters 134 may also include a 30-nanometer cap of silicon nitride. The heaters 134 may be formed by depositing multiple thin-film layers in succession. A stack of thin-film layers combine the elementary properties of the individual layers.

A ratio of an area of the heater 134 to an area of the nozzle 130 may be greater than seven to one. The heater 134 may be square, with each side having a length 147. The length may be 47 microns, 51 microns, or 71 microns. This would have an area of 2209, 2601, or 5041 microns square, respectively. If the nozzle diameter is 20 microns, an area at the second end would be 314 microns square, giving an approximate ratio of 7 to 1, 8 to 1, or 16 to 1, respectively.

Figure 23:
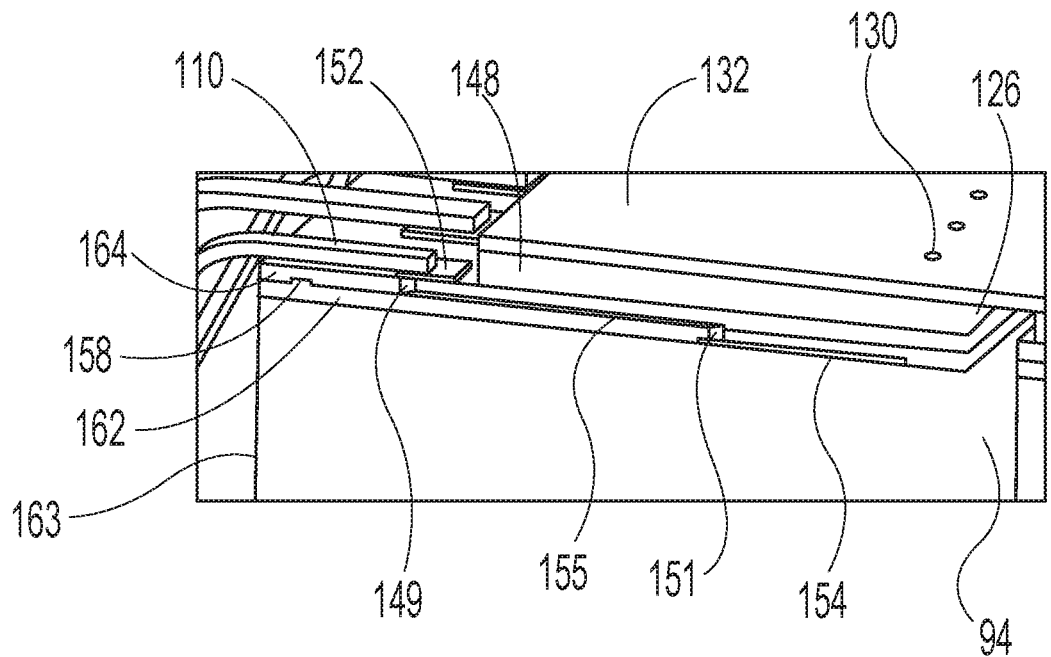
FIG. 23 is a sectional view of FIG. 17 taken along lines 23-23.

With reference to FIG. 23, a length of the first contact 154 can be seen adjacent to the inlet 94. A via 151 couples the first contact 154 to trace 155 that is formed on the first dielectric layer 162. The second dielectric layer 164 is on the trace 155. A via 149 is formed through the second dielectric layer 164 and couples the trace 155 to the contact pad 152. A portion of the ground line 158 is visible toward an edge 163 of the die, between the via 149 and the edge 163.

The microfluidic die 92 may be relatively simple and free of complex integrated circuitry. This microfluidic die 92 will be controlled and driven by an external microcontroller or microprocessor. The external microcontroller or microprocessor may be provided in the housing. This allows the PCB 106 and the microfluidic die 92 to be simplified and cost effective. There may be two metal or conductive levels formed on the substrate. These conductive levels include the contact 154 and the trace 155. All of these features can be formed on a single metal level. This allows the microfluidic die to be simple to manufacture and minimizes the number of layers of dielectric between the heater and the chamber.

With reference to FIG. 16, the opening 78 of the microfluidic delivery member 64 may include a liner 100 that covers exposed sidewalls 102 of the PCB 106. The liner 100 may be any material configured to protect the PCB 106 from degradation due to the presence of the fluid composition, such as to prevent fibers of the board from separating. In that regard, the liner 100 may protect against particles from the PCB 106 entering into the fluid path and blocking the nozzles 130. For instance, the opening 78 may be lined with a material that is less reactive to the fluid composition in the reservoir than the material of the PCB 106. In that regard, the PCB 106 may be protected as the fluid composition passes therethrough. The through hole may be coated with a metal material, such as gold.

Sensors

The microfluidic delivery device may include commercially available sensors that respond to environmental stimuli such as light, noise, motion, and/or odor levels in the air. For example, the microfluidic delivery device can be programmed to turn on when it senses light, and/or to turn off when it senses no light. In another example, the microfluidic delivery device can turn on when the sensor senses a person moving into the vicinity of the sensor. Sensors may also be used to monitor the odor levels in the air. The odor sensor can be used to turn-on the microfluidic delivery device, increase the heat or fan speed, and/or step-up the delivery of the fluid composition from the microfluidic delivery device when it is needed.

VOC sensors can be used to measure intensity of perfume from adjacent or remote devices and alter the operational conditions to work synergistically with other perfume devices. For example a remote sensor could detect distance from the emitting device as well as fragrance intensity and then provide feedback to the microfluidic delivery device on where to locate the microfluidic delivery device to maximize room fill and/or provide the "desired" intensity in the room for the user.

The microfluidic delivery devices may communicate with each other and coordinate operations in order to work synergistically with other perfume delivery devices.

The sensor may also be used to measure fluid composition levels in the reservoir or count firing of the heating elements to indicate the cartridge's end-of-life in advance of depletion. In such case, an LED light may turn on to indicate the reservoir needs to be filled or replaced with a new reservoir.

The sensors may be integral with the microfluidic delivery device housing or in a remote location (i.e. physically separated from the microfluidic delivery device housing) such as remote computer or mobile smart device/phone. The sensors may communicate with the microfluidic delivery device remotely via low energy blue tooth, 6 low pan radios or any other means of wirelessly communicating with a device and/or a controller (e.g. smart phone or computer).

The user may be able to change the operational condition of the device remotely via low energy blue tooth, or other means.

Smart Chip

The cartridge 26 may include a memory in order to transmit optimal operational condition to the microfluidic delivery device.

Fluid Composition

To operate satisfactorily in a microfluidic delivery device, many characteristics of a fluid composition are taken into consideration. Some factors include formulating fluid compositions with viscosities that are optimal to emit from the microfluidic delivery member, formulating fluid compositions with limited amounts or no suspended solids that would clog the microfluidic delivery member, formulating fluid compositions to be sufficiently stable to not dry and clog the microfluidic delivery member, formulating fluid compositions that are not flammable, etc. For adequate dispensing from a microfluidic die, proper atomization and effective delivery of an air freshening or malodor reducing composition may be considered in designing a fluid composition.

The fluid composition may comprise a perfume composition.

The fluid composition may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the fluid composition may have surface tensions below about 35, alternatively from about 20 to about 30 dynes per centimeter. Viscosity is in cps, as determined using a TA Instrument Rheometer: Model AR-G2 (Discovery HR-2) with a single gap stainless steel cup and bob under the following conditions:

Settings:
Temperature 25° C.
Duration 60.0 s
Strain % 2%
Angular frequency 10 rad/s
Geometry: 40 mm parallel Plate (Peltier Plate Steel)
Run Procedure Information:
Conditioning
   temperature 25 C
   no pre-shear
   equilibration 2 minutes
Steady State Flow
ramp 1-100 1/s
mode-log
5 points/decade
sample period 10 seconds
5% tolerance with 3 consecutive within tolerance The fluid composition may be substantially free of suspended solids or solid particles existing in a mixture wherein particulate matter is dispersed within a liquid matrix. The fluid composition may have less than 5 wt. % of suspended solids, alternatively less than 4 wt. % of suspended solids, alternatively less than 3 wt. % of suspends, alternatively less than 2 wt. % of suspended solids, alternatively less than 1 wt. % of suspended solids, alternatively less than 0.5 wt. % of suspended solids, or free of suspended solids. Suspended solids are distinguishable from dissolved solids that are characteristic of some perfume materials.

It is contemplated that the fluid composition may comprise other volatile materials in addition to or in substitution for the perfume mixture including, but not limited to, volatile dyes; compositions that function as insecticides or insect repellants; essential oils or materials that acts to condition, modify, or otherwise modify the environment (e.g. to assist with sleep, wake, respiratory health, and like conditions); deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

Perfume Mixture

The fluid composition may contain a perfume mixture present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. The fluid composition may consist entirely of the perfume mixture (i.e. 100 wt. %).

The perfume mixture may contain one or more perfume raw materials. The raw perfume materials are selected based on the material's boiling point ("B.P."). The B.P. referred to herein is the boiling point under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969. Where the experimentally measured boiling point of individual components is not available, the value may be estimated by the boiling point PhysChem model available from ACD/Labs (Toronto, Ontario, Canada).

The perfume mixture may have a mol-weighted average log of the octanol-water partitioning coefficient ("ClogP") of less than about 2.9, alternatively less than about 2.5, alternatively less than about 2.0. Where the experimentally measured log P of individual components is not available, the value may be estimated by the boiling point PhysChem model available from ACD/Labs (Toronto, Ontario, Canada).

The perfume mixture may have a mol-weighted average B.P. of less than 250° C., alternatively less than 225° C., alternatively less than 200° C., alternatively less than about 150° C., or alternatively about 150° C. to about 250° C.

Alternatively, about 3 wt % to about 25 wt % of the perfume mixture may have a mol-weighted average B.P. of less than 200° C., alternatively about 5 wt % to about 25 wt % of the perfume mixture has a mol-weighted average B.P. of less than 200° C.

For purposes of the present disclosure, the perfume mixture boiling point is determined by the mole-weighted average boiling point of the individual perfume raw materials making up said perfume mixture. Where the boiling point of the individual perfume materials is not known from published experimental data, it is determined by the boiling point PhysChem model available from ACD/Labs.

Table 1 lists some non-limiting, exemplary individual perfume materials suitable for the perfume mixture.

TABLE 1

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 40-82-6 | Eucalyptol | 175 |
| 141-78-6 | Ethyl acetate | 77 |

Table 2 shows an exemplary perfume mixture having a total molar weighted average B.P. ("mol-weighted average boiling point") less than 200° C. In calculating the mol-weighted average boiling point, the boiling point of perfume raw materials that may be difficult to determine, may be neglected if they comprise less than 15% by weight of the total perfume mixture, as exemplified in Table 2.

TABLE 2

| CAS Number | Perfume Raw Material Name | Wt % | Molecular Weight | Mol % | B.P. (° C.) |
|---|---|---|---|---|---|
| 123-68-2 | Allyl Caproate | 2.50 | 156.2 | 2.6 | 185 |
| 140-11-4 | Benzyl Acetate | 3.00 | 150.2 | 3.3 | 214 |
| 928-96-1 | Beta Gamma Hexenol | 9.00 | 100.2 | 14.8 | 157 |
| 18479-58-8 | Dihydro Myrcenol | 5.00 | 156.3 | 5.3 | 198 |
| 39255-32-8 | Ethyl 2 Methyl Pentanoate | 9.00 | 144.2 | 10.3 | 157 |
| 77-83-8 | Ethyl Methyl Phenyl Glycidate | 2.00 | 206.2 | 1.6 | 260 |
| 7452-79-1 | Ethyl-2-Methyl Butyrate | 8.00 | 130.2 | 10.1 | 132 |
| 142-92-7 | Hexyl Acetate | 12.50 | 144.2 | 14.3 | 146 |
| 68514-75-0 | Orange Phase Oil 25X1.18%-Low Cit. 14638 | 10.00 | mixture | neglected | 177 |
| 93-58-3 | Methyl Benzoate | 0.50 | 136.1 | 0.6 | 200 |
| 104-93-8 | Para Cresyl Methyl Ether | 0.20 | 122.2 | 0.3 | 176 |
| 1191-16-8 | Prenyl Acetate | 8.00 | 128.2 | 10.3 | 145 |
| 88-41-5 | Verdox | 3.00 | 198.3 | 2.5 | 223 |
| 58430-94-7 | Iso Nonyl Acetate | 27.30 | 186.3 | 24.1 | 225 |
| | TOTAL: | 100.00 | | 100.0 | |
| | Mol-weighted average B.P. | | | | 176.4 |

Water

The fluid composition may comprise water. The fluid composition may comprise water in an amount from about 0.25 wt. % to about 9.5 wt. % water, alternatively about 0.25 wt. % to about 7.0 wt. % water, alternatively about 1% to about 5% water, alternatively from about 1% to about 3% water, alternatively from about 1% to about 2% water, by weight of the fluid composition. Without wishing to be bound by theory, it has been found that by formulating the perfume mixture to have a mol-weighted average ClogP of less than about 2.5, water can be incorporated into the fluid composition at a level of about 0.25 wt. % to about 9.5 wt. %, alternatively about 0.25 wt. % to about 7.0 wt. %, by weight of the overall composition.

Oxygenated Solvent

The fluid composition may contain one or more oxygenated solvent such as a polyol (components comprising more than one hydroxyl functionality), a glycol ether, or a polyether.

Exemplary oxygenated solvents comprising polyols include ethylene glycol, diethylene glycol, triethylene glycol, propylene glycol, dipropylene glycol, and/or glycerin. The polyol used in the freshening composition of the present invention may be, for example glycerin, ethylene glycol, propylene glycol, dipropylene glycol.

Exemplary oxygenated solvents comprising polyethers are polyethylene glycol, and polypropylene glycol Exemplary oxygenated solvents comprising glycol ethers are propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycol phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. The oxygenated solvent may be ethylene glycol, propylene glycol, or mixtures thereof. The glycol used may be diethylene glycol.

The oxygenated solvent may be added to the composition at a level of from about 0.01 wt. % to about 20 wt. %, by weight of the composition, alternatively from about 0.05 wt. % to about 10 wt. %, alternatively from about 0.1 wt. % to about 5 wt. %, by weight of the overall composition.

The fluid composition may comprise a perfume mixture, a polyol, and water. In such compositions, it is preferable that the fluid composition comprise from about 50% to about 100%, by weight of the fluid composition, of a perfume mixture, a polyol; and from about 0.25 wt. % to about 9.5 wt. % water, alternatively about 0.25 wt. % to about 7.0 wt. % water, by weight of the fluid composition. Without wishing to be bound by theory, it is believed that the addition of water the fluid composition comprising a perfume mixture reduces the boiling point of the fluid composition, which in turn reduces the energy or heat needed to atomize the fluid composition. As a result of a reduced firing temperature on the heater of the die, it is believed that less fluid composition and less decomposition products of the fluid composition build up on the heater. Moreover, it is believed that water increases the spray rate by dispensing more of the fluid composition in the nozzle at each firing, which results in fewer firings out of each nozzle of the microfluidic die or a reduced number of required nozzles for the desired spray rate, resulting in an increased life to the nozzles. In order to facilitate incorporation of water, the perfume mixture may have a molar weighted average ClogP of less than about 2.9.

Functional Perfume Components

The fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs aid in the evaporation of perfume materials and may provide a hedonic, fragrance benefit. FPCs may be used in relatively large concentrations without negatively impacting perfume character of the overall composition. As such, the fluid composition may be substantially free of VOCs, meaning it has no more than 18%, alternatively no more than 6%, alternatively no more than 5%, alternatively no more than 1%, alternatively no more than 0.5%, by weight of the composition, of VOCs. The fluid composition may be free of VOCs.

Perfume materials that are suitable as a FPC may have a KI, as defined above, from about 800 to about 1500, alternatively about 900 to about 1200, alternatively about 1000 to about 1100, alternatively about 1000.

Perfume materials that are suitable for use as a FPC can also be defined using odor detection threshold ("ODT") and non-polarizing scent character for a given perfume character scent camp. ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment:
  GC: 5890 Series with FID detector (Agilent Technologies, Ind., Palo Alto, California, USA);
  7673 Autosampler (Agilent Technologies, Ind., Palo Alto, California, USA);
  Column: DB-1 (Agilent Technologies, Ind., Palo Alto, California, USA) Length 30 meters ID 0.25 mm film thickness 1 micron (a polymer layer on the inner wall of the capillary tubing, which provide selective partitioning for separations to occur).

Method Parameters:
  Split Injection: 17/1 split ratio;
  Autosampler: 1.13 microliters per injection;

Column Flow: 1.10 mL/minute;
Air Flow: 345 mL/minute;
Inlet Temp. 245° C.;
Detector Temp. 285° C.
Temperature Information:
Initial Temperature: 50° C.;
Rate: 5 C/minute;
Final Temperature: 280° C.;
Final Time: 6 minutes;
Leading assumptions: (i) 12 seconds per sniff
 (ii) GC air adds to sample dilution.

FPCs may have an ODT from greater than about 1.0 parts per billion ("ppb"), alternatively greater than about 5.0 ppb, alternatively greater than about 10.0 ppb, alternatively greater than about 20.0 ppb, alternatively greater than about 30.0 ppb, alternatively greater than about 0.1 parts per million.

The FPCs in a fluid composition may have a KI in the range from about 900 to about 1400; alternatively from about 1000 to about 1300. These FPCs can be either an ether, an alcohol, an aldehyde, an acetate, a ketone, or mixtures thereof.

FPCs may be volatile, low B.P. perfume materials. Exemplary FPC include iso-nonyl acetate, dihydro myrcenol (3-methylene-7-methyl octan-7-ol), linalool (3-hydroxy-3, 7-dimethyl-1, 6 octadiene), geraniol (3, 7 dimethyl-2, 6-octadien-1-ol), d-limonene (1-methyl-4-isopropenyl-1-cyclohexene, benzyl acetate, isopropyl mystristate, and mixtures thereof. Table 3 lists the approximate reported values for exemplary properties of certain FPCs.

TABLE 3

| FPC | B.P. (° C.) | MW | Clog P @ 25° C. | Flash point (° C.) | Vapor pressure | KI | ODT |
|---|---|---|---|---|---|---|---|
| Iso-Nonyl Acetate (CAS# 58430-94-7) | 225 | 186.3 | 4.28 | 79.4 | 0.11 | 1178 | 12 ppb |
| Dihydro Myrcenol (CAS# 18479-58-8) | 198 | 156.3 | 3.03 | 76.1 | 0.1 | 1071 | 32 ppb |
| Linalool (CAS# 78-70-6) | 205 | 154.3 | 2.549 | 78.9 | 0.05 | 1107 | 22 ppb |
| Geraniol (CAS# 106-24-1) | 237 | 154.3 | 2.769 | 100 | 0.00519 | 1253 | 0.4 ppb |
| D-Limonene (CAS# 94266-47-4) | 170 | 136 | 4.35 | 47.2 | 1.86 | 1034 | 204 ppb |

The total amount of FPCs in the perfume mixture may be greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 75% to about 100%, alternatively from about 80% to about 100%, alternatively from about 85% to about 100%, alternatively from about 90% to about 100%, alternatively about 100%, by weight of the perfume mixture. The perfume mixture may consist entirely of FPCs (i.e. 100 wt. %).

Table 4 lists a non-limiting, exemplary fluid composition comprising FPCs and their approximate reported values for KI and B.P.

TABLE 4

| Material Name | KI | wt. % | B.P. (° C.) |
|---|---|---|---|
| Benzyl Acetate (CAS # 140-11-4) | 1173 | 1.5 | 214 |
| Ethyl-2-methyl Butyrate (CAS # 7452-79-1) | 850 | 0.3 | 132 |
| Amyl Acetate (CAS # 628-63-7) | 912 | 1.0 | 149 |
| Cis 3 Hexenyl Acetate (CAS # 3681-71-8) | 1009 | 0.5 | 169 |
| Ligustral (CAS # 27939-60-2) | 1094 | 0.5 | 177 |
| Melonal (CAS # 106-72-9) | 1060 | 0.5 | 116 |
| Hexyl Acetate (CAS # 142-92-7) | 1016 | 2.5 | 146 |
| Dihydro Myrcenol (CAS# 18479-58-8) | 1071 | 15 | 198 |
| Phenyl Ethyl Alcohol (CAS# 60-12-8) | 1122 | 8 | 219 |
| Linalool (CAS # 78-70-6) | 1243 | 25.2 | 205 |
| Geraniol (CAS# 106-24-1) | 1253 | 5 | 238 |
| Iso Nonyl Acetate (CAS# 40379-24-6) | 1295 | 22.5 | 225 |
| Benzyl Salicylate (CAS # 118-58-1) | 2139 | 3 | 320 |
| Coumarin (CAS # 91-64-5) | 1463 | 1.5 | 267 |
| Methyl Dihydro Jasmonate (CAS# 24851-98-7) | 1668 | 7 | 314 |
| Hexyl Cinnamic Aldehyde (CAS # 101-86-0) | 1770 | 6 | 305 |

When formulating fluid compositions, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

Method of Use

The microfluidic delivery device 10 may be used to deliver a fluid composition into the air. The microfluidic delivery device 10 may also be used to deliver a fluid composition into the air for ultimate deposition on one or more surfaces in a space. Exemplary surfaces include hard surfaces such as counters, appliances, floors, and the like. Exemplary surfaces also include carpets, furniture, clothing, bedding, linens, curtains, and the like. The microfluidic delivery device may be used in homes, offices, businesses, open spaces, cars, temporary spaces, and the like. The microfluidic delivery device may be used for freshening, malodor removal, insect repellant, and the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A microfluidic delivery device defining a longitudinal axis and a lateral axis, the microfluidic delivery device comprising:
   a housing electrically connectable with a power source, wherein the housing comprises an interior and an exterior;
   a cartridge releasably connectable with the housing, wherein the cartridge comprises a reservoir for containing a fluid composition and a microfluidic die in fluid communication with the reservoir, wherein the reservoir comprises a top surface, a bottom surface opposing the top surface, and a sidewall that joins the top surface and the bottom surface, wherein the sidewall is parallel with the longitudinal axis, wherein the microfluidic die is disposed on the sidewall proximate the bottom surface and is configured to dispense a fluid composition from a fluid outlet disposed on the sidewall;
   a fan; and
   an air flow channel extending from the fan to an air outlet in the housing, wherein:
      the device is configured such that the fluid composition exiting the fluid outlet converges with air flow exiting the air outlet at the exterior of the housing such that the fluid composition is redirected from a first direction to a second direction,
   the first direction is not substantially upward along the longitudinal axis, and
   the second direction is substantially upward along the longitudinal axis.

2. The microfluidic delivery device of claim 1, wherein air flow exiting the air outlet travels upward relative to horizontal.

3. The microfluidic delivery device of claim 1, wherein the air flow channel comprises a screen.

4. The microfluidic delivery device of claim 1, wherein the microfluidic die comprises a piezoelectric crystal or a heater.

5. The microfluidic delivery device of claim 1, wherein the cartridge is disposed at least partially within the housing.

6. The microfluidic delivery device of claim 1, wherein the cartridge comprises a sponge.

7. The microfluidic delivery device of claim 1, wherein the fluid composition comprises perfume.

* * * * *